US010265315B2

(12) United States Patent
O'Malley et al.

(10) Patent No.: US 10,265,315 B2
(45) Date of Patent: Apr. 23, 2019

(54) SMALL MOLECULE REGULATORS OF STEROID RECEPTOR COACTIVATORS AND METHODS OF USE THEREOF

(71) Applicant: BAYLOR COLLEGE OF MEDICINE, Houston, TX (US)

(72) Inventors: Bert W. O'Malley, Houston, TX (US); David Michael Lonard, Pearland, TX (US); Jin Wang, Sugar Land, TX (US); Jianming Xu, Bellaire, TX (US); Jianwei Chen, Houston, TX (US)

(73) Assignee: BAYLOR COLLEGE OF MEDICINE, Houston, TX (US)

( * ) Notice: Subject to any disclaimer, the term of this patent is extended or adjusted under 35 U.S.C. 154(b) by 0 days.

(21) Appl. No.: 15/480,731

(22) Filed: Apr. 6, 2017

(65) Prior Publication Data

US 2017/0290830 A1  Oct. 12, 2017

Related U.S. Application Data

(60) Provisional application No. 62/320,121, filed on Apr. 8, 2016, provisional application No. 62/441,658, filed on Jan. 3, 2017.

(51) Int. Cl.

| | |
|---|---|
| C07D 401/12 | (2006.01) |
| C07D 403/12 | (2006.01) |
| A61K 31/506 | (2006.01) |
| A61K 31/4184 | (2006.01) |
| A61K 31/426 | (2006.01) |
| A61K 31/4402 | (2006.01) |
| C07D 401/14 | (2006.01) |
| C07D 405/12 | (2006.01) |
| C07D 409/12 | (2006.01) |
| C07D 413/12 | (2006.01) |
| C07D 417/12 | (2006.01) |
| C07D 471/04 | (2006.01) |
| C07D 487/04 | (2006.01) |
| C07D 498/04 | (2006.01) |

(52) U.S. Cl.
CPC ........ *A61K 31/506* (2013.01); *A61K 31/4184* (2013.01); *A61K 31/426* (2013.01); *A61K 31/4402* (2013.01); *C07D 401/12* (2013.01); *C07D 401/14* (2013.01); *C07D 403/12* (2013.01); *C07D 405/12* (2013.01); *C07D 409/12* (2013.01); *C07D 413/12* (2013.01); *C07D 417/12* (2013.01); *C07D 471/04* (2013.01); *C07D 487/04* (2013.01); *C07D 498/04* (2013.01)

(58) Field of Classification Search
CPC ......................... C07D 401/12; C07D 403/12
See application file for complete search history.

(56) References Cited

U.S. PATENT DOCUMENTS

| | | | | |
|---|---|---|---|---|
| 3,525,622 | A * | 8/1970 | Willems | ................... C09B 26/02 |
| | | | | 430/591 |
| 3,907,700 | A | 9/1975 | Grier | |
| 7,112,680 | B2 * | 9/2006 | Hofmann | ............. C07D 401/12 |
| | | | | 546/273.4 |
| 8,440,705 | B2 * | 5/2013 | Lindquist | ............. A61K 31/522 |
| | | | | 514/367 |
| 2003/0166658 | A1 | 9/2003 | Hofmann et al. | |
| 2006/0264627 | A1 | 11/2006 | Hofmann et al. | |
| 2015/0374662 | A1 | 12/2015 | Bode et al. | |

FOREIGN PATENT DOCUMENTS

| | | |
|---|---|---|
| WO | 2001094340 A1 | 12/2001 |
| WO | 20110161159 A1 | 12/2011 |

OTHER PUBLICATIONS

Chemical Abstracts Registry No. 3718-05-6, indexed in the Registry file in STN CAS Online on Nov. 16, 1984.*
Chemical Abstracts Registry No. 452320-04-6, indexed in the Registry file on STN CAS Online Sep. 18, 2002.*
Chemical Abstracts Registry No. 1424660-84-3, indexed in the Registry file on STN CAS Online Mar. 18, 2013.*
Chemical Abstracts Registry No. 1799095-85-4, indexed in the Registry file on STN CAS Online Jul. 12, 2015.*
Chemical Abstracts Registry No. 109-66-0, indexed in the Registry file on STN CAS Online Nov. 16, 1984.*
Easmon et al., "2-benzoxazolyl and 2-benzimidazolyl hydrazones derived from 2-acetylpyridine: A novel class of antitumor agents", Int. J. Cancer, vol. 94 No. 1, pp. 89-96, Oct. 1, 2001.
Ertl et al., "Fast calculation of molecular polar surface area as a sum of fragment-based contributions and its application to the prediction of drug transport properties", Journal of Medicinal Chemistry, vol. 43 No. 20, pp. 3714-3717, Oct. 5, 2000.
Kerns et al., "Drug-like properties: Concepts, structure design and methods from ADME to toxicity optimization", Academic Press, 2010.
Lonard et al., "The 26S proteasome is required for estrogen receptor-alpha and coactivator turnover and for efficient estrogen receptor-alpha transactivation", Molecular Cell, vol. 5 No. 6, pp. 939-948, Jun. 2000.
Marques et al., "Simulated biological fluids with possible application in dissolution testing", Dissolution Technol., vol. 18 No. 3, pp. 15-28, Aug. 31, 2011.
Newman et al., "Cardiac glycosides as novel cancer therapeutic agents", Molecular Interventions, vol. 8 No. 1, pp. 36-49, Feb. 2008.

(Continued)

*Primary Examiner* — Laura L Stockton
(74) *Attorney, Agent, or Firm* — Kilpatrick Townsend & Stockton LLP

(57) ABSTRACT

Small molecule regulators of steroid receptor coactivator (SRC) family proteins are provided, as well as methods for their use in treating or preventing SRC-related diseases. The SRC-related diseases can include cancer, metabolic disorders, human immunodeficiency virus, neurodegenerative disorders, and/or inflammatory diseases. Also provided are methods for regulating SRC family proteins in a cell.

27 Claims, 4 Drawing Sheets

(56) References Cited

OTHER PUBLICATIONS

Prassas et al., "Novel therapeutic applications of cardiac glycosides", Nat Rev Drug Discov., vol. 7 No. 11, pp. 926-935, Nov. 2008.
Veber et al., "Molecular properties that influence the oral bioavailability of drug candidates", Journal of Medicinal Chemistry, vol. 45 No. 12, pp. 2615-2623, Jun. 6, 2002.
Wang et al., "Small molecule inhibition of the steroid receptor coactivators, SRC-3 and SRC-1", Molecular Endocrinology, vol. 25 No. 12, pp. 2041-2053, Dec. 2011.
Aldib et al., "Evaluation of new scaffolds of myeloperoxidase inhibitors by rational design combined with high-throughput virtual screening", Journal of Medicinal Chemistry, vol. 55, No. 16, pp. 7208-7218, Jul. 13, 2012.
Arkin et al., "Small-molecule inhibitors of protein-protein interactions: progressing towards the dream", Nature Reviews Drug Discovery, vol. 3 No. 4, pp. 301-317, Apr. 2004.
Arnold et al., "Discovery of small molecule inhibitors of the interaction of the thyroid hormone receptor with transcriptional coregulators", The Journal of Biological Chemistry, vol. 280 No. 52, pp. 43048-43055, Dec. 30, 2005.
Basarab et al., "Fragment-to-hit-to-lead discovery of a novel pyridylurea scaffold of ATP competitive dual targeting type II topoisomerase inhibiting antibacterial agents", Journal of Medicinal Chemistry, vol. 56, No. 21, pp. 8712-8735, Oct. 7, 2013.
Bowlby et al., "hERG (KCNH2 or Kv11.1) K+ channels: screening for cardiac arrhythmia risk", Current Drug Metabolism, vol. 9 No. 9, pp. 965-970, Nov. 2008.
Campbell et al., "In silico characterization of an atypical MAPK phosphatase of plasmodium falciparum as a suitable target for drug discovery", Chem Biol Drug Des., vol. 84 No. 2, pp. 158-168, 2014.
Chang et al., "Dissection of the LXXLL nuclear receptor-coactivator interaction motif using combinatorial peptide libraries: discovery of peptide antagonists of estrogen receptors alpha and beta", Mol Cell Biol., vol. 19 No. 12, Dec. 1999, pp. 8226-8239.
Chopra et al., "Cellular energy depletion resets whole-body energy by promoting coactivator-mediated dietary fuel absorption", Cell Metab., vol. 13 No. 1, pp. 35-43, Jan. 5, 2011.
Clackson et al., "A hot spot of binding energy in a hormone-receptor interface", Science, vol. 267 No. 5196, pp. 383-386, Jan. 20, 1995.
Dasgupta et al., "Nuclear receptor coactivators: master regulators of human health and disease", Annu Rev Med., vol. 65, pp. 279-292, 2014.
Dorn et al., "Evaluation of a high-throughput fluorescence assay method for HERG potassium channel inhibition", J Biomol Screen, vol. 10 No. 4, pp. 339-347, 2005.
Frese et al., "Cardiac glycosides initiate Apo2L/TRAIL-induced apoptosis in non-small cell lung cancer cells by up-regulation of death receptors 4 and 5", Cancer Res., vol. 66 No. 11, pp. 5867-5874, Jun. 1, 2006.
Fu et al., "Aberrantly elevated microRNA-34a in obesity attenuates hepatic responses to FGF19 by targeting a membrane coreceptor beta-Klotho", Proc Natl Acad Sci USA, vol. 109 No. 40, pp. 16137-16142, Oct. 2, 2012.
Gemma et al., "Quinolylhydrazones a novel inhibitors of plasmodium falciparum serine protease PfSUB1", Bioorganic & Medicinal Chemistry Letters, vol. 22 No. 16, Jun. 23, 2012.
Hall et al., "Investigations on the mechanism of action of the novel antitumor agents 2-benzothiazolyl, 2-benzoxazolyl, and 2-benzimidazolyl hydrazones derived from 2-acetylpyridine", Arch. Pharm Pharm Med Chem., vol. 332, pp. 115-123, 1999.
Hann et al., "Pursuing the leadlikeness concept in pharmaceutical research", Current Opinion in Chemical Biology, vol. 8 No. 3, pp. 255-263, Jun. 2004.
Huh et al., "Digoxin and its derivatives suppress TH17 cell differentiation by antagonizing RORgammat activity", Nature, vol. 472 No. 7344, pp. 486-490, Apr. 28, 2011.
Johnson et al., "Steroid receptor coactivators 1, 2, and 3: Critical regulators of nuclear receptor activity and steroid receptor modulator (SRM)-based cancer therapy", Mol Cell Endocrinol., vol. 348 No. 2, pp. 430-439, Jan. 30, 2012.
Jordan, "Selective estrogen receptor modulation: Concept and consequences in cancer", Cancer Cell, vol. 5 No. 3, pp. 207-213, Mar. 2004.
Jordan, "Tamoxifen: a most unlikely pioneering medicine", Nat Rev Drug Discov., vol. 2 No. 3, pp. 205-213, Mar. 2003.
Kwon et al., "Geometrical isomers of the hydrazones from 2-formyl, 2-acetyl- and 2-benzoylpyridine and 2-hydrazinobenzothiazole", Nippon Kagaku Kaishi: The Chemical Society of Japan, No. 7, pp. 1314-1319, 1973.
Lipinski et al., "Experimental and computational approaches to estimate solubility and permeability in drug discovery and development settings", Adv Drug Deliv Rev., vol. 46 Nos. 1-3, pp. 3-26, Mar. 1, 2001.
Lo Conte et al., "The atomic structure of protein-protein recognition sites", Journal of Molecular Biology, vol. 285 No. 5, pp. 2177-2198, Feb. 5, 1999.
Lonard et al., "Nuclear receptor coregulators: modulators of pathology and therapeutic targets", Nature Reviews, Endocrinology, vol. 8 No. 10, pp. 598-604, Oct. 2012.
Lonard et al., "SRC-3 transcription-coupled activation, degradation, and the ubiquitin clock: is there enough coactivator to go around in cells", Science Signaling, vol. 1 No. 13, pp. pe16, Apr. 1, 2008.
Lonard et al., "The expanding cosmos of nuclear receptor coactivators", Cell, vol. 125 No. 3, pp. 411-414, May 5, 2006.
Manna et al., "Oleandrin suppresses activation of nuclear transcription factor-kappaB, activator protein-1, and c-Jun NH2-terminal kinase", Cancer Res., vol. 60 No. 14, pp. 3838-3847, Jul. 15, 2000.
Menger et al., "Cardiac glycosides exert anticancer effects by inducing immunogenic cell death", Science Translational Medicine, vol. 4 No. 143, pp. 143ra199, Jul. 18, 2012.
Mijatovic et al., "The cardenolide UNBS1450 is able to deactivate nuclear factor kappaB-mediated cytoprotective effects in human non-small cell lung cancer cells", Molecular Cancer Therapeutics, vol. 5 No. 2, pp. 391-399, Feb. 2006.
Minn et al., "Genes that mediate breast cancer metastasis to lung", Nature, vol. 436 No. 7050, pp. 518-524, Jul. 28, 2005.
Norris et al., "Peptide antagonists of the human estrogen receptor", Science, vol. 285 No. 5428, Jul. 30, 1999, pp. 744-746.
Ogawa et al., "Crystal structure of the sodium-potassium pump (Na+,K+-ATPase) with bound potassium and ouabain", Proc Natl Acad Sci USA, vol. 106 No. 33, pp. 13742-13747, Aug. 18, 2009.
Onate et al., "Sequence and characterization of a coactivator for the steroid hormone receptor superfamily", Science, vol. 270 No. 5240, pp. 1354-1357, Nov. 24, 1995.
Pervova et al., "Synthesis, structure, and photochemical properties of hetarylaldehydes benzimidazolyl-2-hydrazones", Russian Journal of General Chemistry, vol. 80 No. 5, pp. 987-993, Sep. 8, 2009.
PCT/US2017/026330, "International Search Report with Written Opinion", dated Jun. 12, 2017, 22 pages.
Platz et al., "A novel two-stage, transdisciplinary study identifies digoxin as a possible drug for prostate cancer treatment", Cancer Discovery, vol. 1 No. 1, pp. 68-77, Jun. 2011.
Pondugula et al., "Pregnane xenobiotic receptor in cancer pathogenesis and therapeutic response", Cancer Letters, vol. 328 No. 1, pp. 1-9, Jan. 1, 2013.
Pubchem, "AC1L94RH", retrieved from https://pubchem.ncbi.nlm.nih.gov/compound/392786#x291, Mar. 26, 2015, 10 pages.
Qin et al., "The AIB1 oncogene promotes breast cancer metastasis by activation of PEA3-mediated matrix metalloproteinase 2 (MMP2) and MMP9 expression", Mol Cell Biol., vol. 28 No. 19, Oct. 2008, pp. 5937-5950.
Sheng et al., "State-of-the-art strategies for targeting protein-protein interactions by small-molecule inhibitors", Chemical Society Reviews, vol. 44 No. 22, pp. 8238-8259, Aug. 6, 2015.
Sleebs et al., "Discovery of potent and selective benzothiazole hydrazine inhibitors of Bcl-$X_L$", Journal of Medicinal Chemistry, vol. 56, pp. 5514-5540, 2013.

(56) References Cited

OTHER PUBLICATIONS

Song et al., "Development of potent small-molecule inhibitors to drug the undruggable steroid receptor coactivator-3", PNAS, vol. 113 No. 18, pp. 4970-4975, May 2, 2016.

Song et al., "Steroid receptor coactivator-3 (SRC-3/AIB1) as a novel therapeutic target in triple negative breast cancer and its inhibition with a phospho-bufalin prodrug", PloS One, vol. 10 No. 10, e0140011, pp. 1-20, Oct. 2, 2015.

Tien et al., "Steroid receptor coactivator-3 as a potential molecular target for cancer therapy", Expert Opinion on Therapeutic Targets, vol. 16 No. 11, pp. 1085-1096, Nov. 2012.

Thorne et al., "Firefly luciferase in chemical biology: A compendium of inhibitors, mechanistic evaluation of chemotypes, and suggested use as a reporter", Chemistry & Biology, vol. 19, pp. 1060-1072, Aug. 24, 2012.

Wang et al., "Bufalin is a potent small molecule inhibitor of the steroid receptor coactivators SRC-3 and SRC-1", Cancer Research, vol. 74 No. 5, pp. 1506-1517, Mar. 1, 2014.

Wang et al., "Characterization of a steroid receptor coactivator small molecule stimulator that overstimulates cancer cells and leads to cell stress and death", Cancer Cell, vol. 28 No. 2, pp. 240-252, Aug. 10, 2015.

Wells et al., "Reaching for high-hanging fruit in drug discovery at protein-protein interfaces", Nature, vol. 450 No. 7172, pp. 1001-1009, Dec. 13, 2007.

Wu et al., "SRC-3 coactivator functional lifetime is regulated by a phospho-dependent ubiquitin time clock", Cell, vol. 129 No. 6, pp. 1125-1140, Jun. 15, 2007.

Xu et al., "Normal and cancer-related functions of the p160 steroid receptor co-activator (SRC) family", Nature Reviews Cancer, vol. 9 No. 9, pp. 615-630, Sep. 2009.

Xu et al., "Review of the in vivo functions of the p160 steroid receptor coactivator family", Molecular Endocrinology, vol. 17 No. 9, pp. 1681-1692, Sep. 2003.

Yan et al., "Identification of verrucarin a as a potent and selective steroid receptor coactivator-3 small molecule inhibitor", PloS One, vol. 9 No. 4:e95243, pp. 1-9, Apr. 17, 2014.

Ye et al., "Cardiac glycosides are potent inhibitors of interferon-beta gene expression", Nature Chemical Biology, vol. 7 No. 1, pp. 25-33, Jan. 2011.

York et al., "Steroid receptor coactivator (SRC) family: masters of systems biology", J Biol Chem, vol. 285 No. 50, pp. 38743-38750, Dec. 10, 2010.

Zhang et al., "Digoxin and other cardiac glycosides inhibit HIF-1alpha synthesis and block tumor growth", Proc Natl Acad Sci USA, vol. 105 No. 50, pp. 19579-19586, Dec. 16, 2008.

Zhang et al., "PKSolver: An add-in program for pharmacokinetic and pharmacodynamic data analysis in microsoft excel", Computer Methods and Programs in Biomedicine, vol. 99 No. 3, pp. 306-314, Feb. 21, 2010.

Zhou et al., "Activation of human ether-a-go-go related gene (hERG) potassium channels by small molecules", Acta Pharmacologica Sinica, vol. 32 No. 6, pp. 781-788, May 30, 2011.

PCT/US2017/026330, "International Preliminary Report on Patentability," dated Oct. 18, 2018, 12 pages.

* cited by examiner

SMALL MOLECULE REGULATORS OF STEROID RECEPTOR COACTIVATORS AND METHODS OF USE THEREOF

CROSS-REFERENCE TO PRIORITY APPLICATIONS

This application claims priority to U.S. Provisional Application Nos. 62/320,121, filed Apr. 8, 2016, and 62/441,658, filed Jan. 3, 2017, which are incorporated herein by reference in their entireties.

STATEMENT REGARDING FEDERALLY FUNDED RESEARCH

This invention was made with government support under Grant Nos. R01GM115622, HD076596, DK059820, and R01CA112403, awarded by the National Institutes of Health, and Grant No. DOD BC120894, awarded by the Department of Defense. The government has certain rights in the invention.

BACKGROUND

Coactivators are non-DNA binding proteins that mediate transcriptional activities of nuclear receptors (NRs) and many other transcription factors. More than 400 coactivators have been identified and associated with a wide range of human diseases, including neurological and metabolic disorders, inflammatory diseases, and cancer. Steroid receptor coactivators contain three family members, including SRC-1, SRC-2 and SRC-3, which function cooperatively to regulate many cellular signaling pathways. Taking estrogen receptor positive (ER+) breast cancer as an example, cancer cells can employ a number of mechanisms to overcome selective estrogen receptor modulators (SERMs) to silence the nuclear receptor (NR) activity. Although breast cancer cells can become resistant to endocrine therapies, it is essential for these cancer cells to recruit coactivators to survive. Coactivators also partner with other transcription factors; therefore, small molecule inhibitors (SMIs) that can directly target the overexpressed coactivators and reduce their activity or stability are targets for drug development. In addition, stimulation of coactivators can be beneficial for certain pathological conditions, including cancer, and can also be beneficial for the treatment of metabolic disorders.

SUMMARY

Described herein are steroid receptor coactivator (SRC) regulators, which are also referred to herein as SRC modulators. Also described herein are methods for their use in treating and/or preventing SRC-related diseases, such as cancer, metabolic disorders (e.g., obesity), human immunodeficiency virus, neurodegenerative disorders, and inflammatory diseases. The methods include administering to a subject a compound as described herein.

A class of steroid receptor coactivator regulators as described herein includes compounds of the following formula:

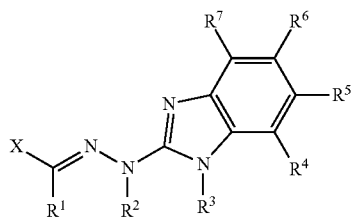

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^1$, $R^4$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^2$ and $R^3$ are each independently selected from hydrogen, substituted or unsubstituted alkyl, or substituted or unsubstituted aryl. In these compounds, when X is a pyridine or a pyrimidine, (1) the pyridine or the pyrimidine is substituted, (2) at least one of $R^4$, $R^5$, $R^6$, and $R^7$ is other than hydrogen, or (3) $R^1$ is other than hydrogen, substituted or unsubstituted alkyl, substituted or unsubstituted aryl, substituted or unsubstituted heteroaryl, or substituted or unsubstituted cycloalkyl.

Optionally, the compound has the following formula:

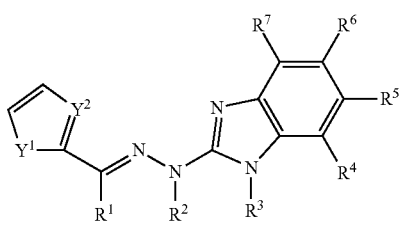

or a pharmaceutically acceptable salt or prodrug thereof, wherein $Y^1$ is CRR, NR, O, or S; and $Y^2$ is CR or N, wherein each R is hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl. In some examples, each R is hydrogen or substituted or unsubstituted alkyl.

Optionally, the compound has the following formula:

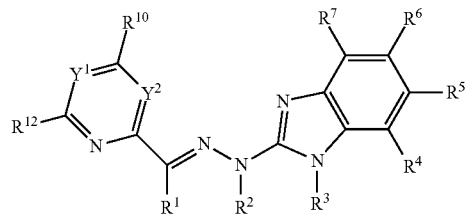

or a pharmaceutically acceptable salt or prodrug thereof, wherein $Y^1$ and $Y^2$ are each independently selected from CR and N, wherein R is hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl; and $R^{10}$ and $R^{12}$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl. In these compounds, at least one of $R^4$, $R^5$, $R^6$, $R^7$, $R^{10}$, $R^{12}$, and R is other than hydrogen. In some examples, R, $R^{10}$, and $R^{12}$ are each independently selected from hydrogen and halogen.

Optionally, the SRC regulator is a compound selected from the group consisting of

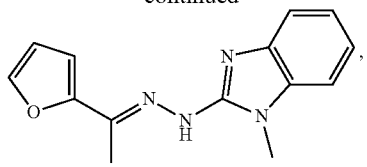

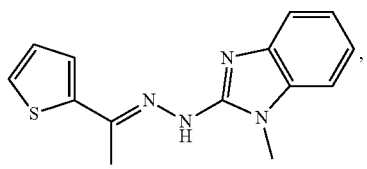

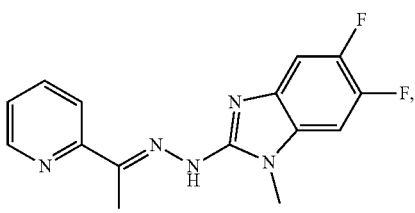

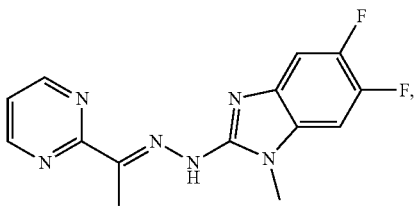

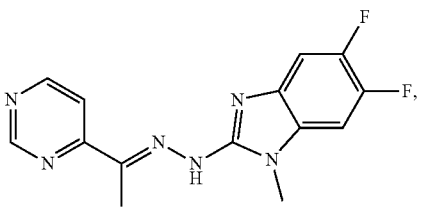

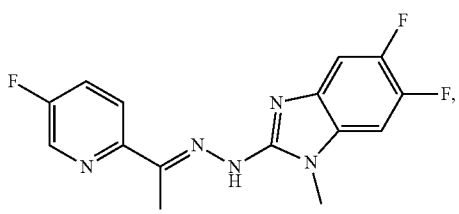

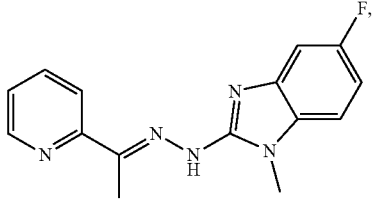

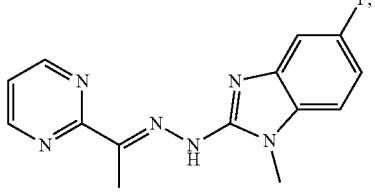

-continued

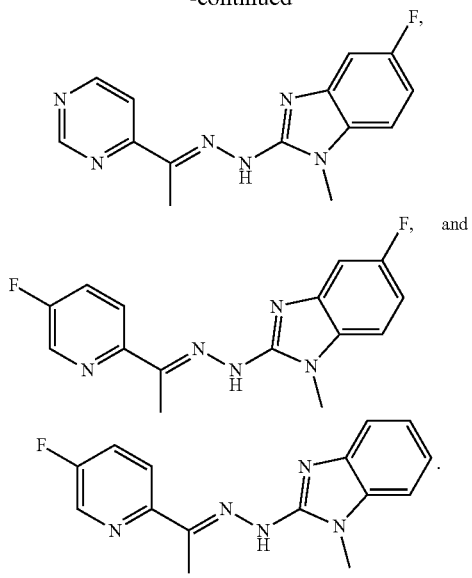

Optionally, the SRC modulator is a tautomer of a compound as described herein. The tautomer can have the following formula:

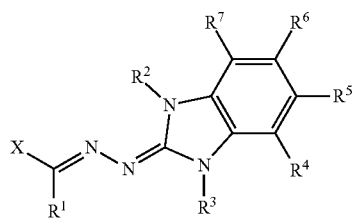

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^1$, $R^4$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^2$ and $R^3$ are each independently selected from hydrogen, substituted or unsubstituted alkyl, and substituted or unsubstituted aryl, wherein when X is a pyridine or a pyrimidine, (1) the pyridine or the pyrimidine is substituted, (2) at least one of $R^4$, $R^5$, $R^6$, and $R^7$ is other than hydrogen, or (3) $R^1$ is other than hydrogen, substituted or unsubstituted alkyl, substituted or unsubstituted aryl, substituted or unsubstituted heteroaryl, or substituted or unsubstituted cycloalkyl.

A class of steroid receptor coactivator regulators as described herein includes compounds of the following formula:

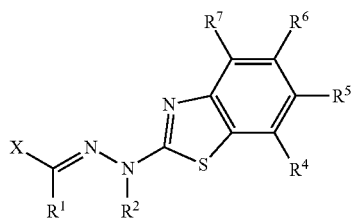

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^1$, $R^4$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^2$ is hydrogen, substituted or unsubstituted alkyl, or substituted or unsubstituted aryl.

A class of steroid receptor coactivator regulators as described herein includes compounds of the following formula:

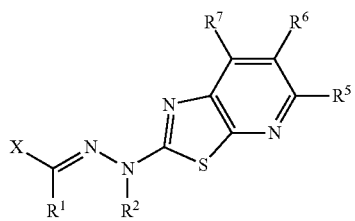

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^1$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^2$ is hydrogen, substituted or unsubstituted alkyl, or substituted or unsubstituted aryl. Optionally, $R^2$ is hydrogen or methyl.

A class of steroid receptor coactivator regulators as described herein includes compounds of the following formula:

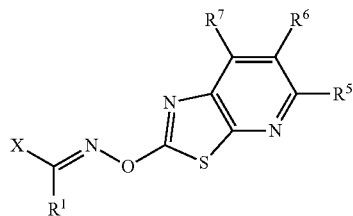

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; and $R^1$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

A class of steroid receptor coactivator regulators as described herein includes compounds of the following formula:

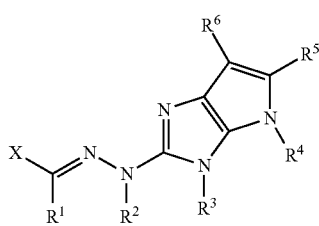

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^1$, $R^5$, and $R^6$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^2$, $R^3$, and $R^4$ are each independently selected from hydrogen, substituted or unsubstituted alkyl, or substituted or unsubstituted aryl.

A class of steroid receptor coactivator regulators as described herein includes compounds of the following formula:

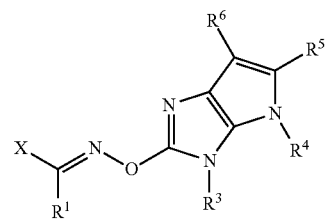

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^1$, $R^5$, and $R^6$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^3$ and $R^4$ are each independently selected from hydrogen, cyano, substituted or unsubstituted alkyl, or substituted or unsubstituted aryl.

A class of steroid receptor coactivator regulators as described herein includes compounds of the following formula:

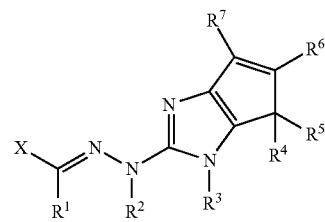

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^1$, $R^4$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^2$ and $R^3$ are each independently selected from hydrogen, substituted or unsubstituted alkyl, or substituted or unsubstituted aryl.

A class of steroid receptor coactivator regulators as described herein includes compounds of the following formula:

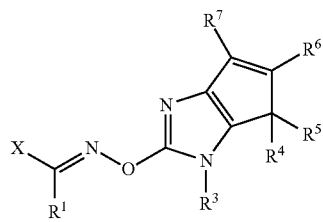

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^1$, $R^4$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^3$ is hydrogen, substituted or unsubstituted alkyl, or substituted or unsubstituted aryl. Optionally, $R^3$ is hydrogen or methyl.

A class of steroid receptor coactivator regulators as described herein includes compounds of the following formula

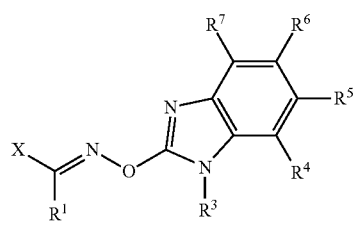

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^1$, $R^4$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^3$ is hydrogen, substituted or unsubstituted alkyl, or substituted or unsubstituted aryl.

A class of steroid receptor coactivator regulators as described herein includes compounds of the following formula:

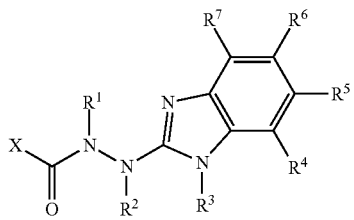

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^1$, $R^2$, and $R^3$ are each independently selected from hydrogen, substituted or unsubstituted alkyl, and substituted or unsubstituted aryl; and $R^4$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

A class of steroid receptor coactivator regulators as described herein includes compounds of the following formula:

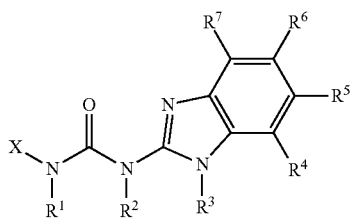

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^1$, $R^2$, and $R^3$ are each independently selected from hydrogen, substituted or unsubstituted alkyl, and substituted or unsubstituted aryl; and $R^4$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

A class of steroid receptor coactivator regulators as described herein includes compounds of the following formula:

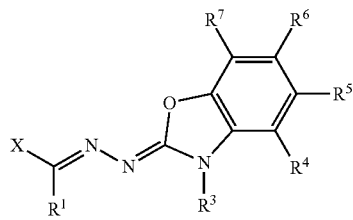

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^1$, $R^4$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^3$ is hydrogen, substituted or unsubstituted alkyl, or substituted or unsubstituted aryl.

A class of steroid receptor coactivator regulators as described herein includes compounds of the following formula:

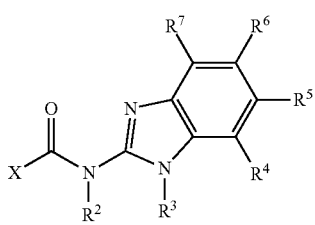

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^2$ and $R^3$ are each independently selected from hydrogen, substituted or unsubstituted alkyl, and substituted or unsubstituted aryl; and $R^4$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

A class of steroid receptor coactivator regulators as described herein includes compounds of the following formula:

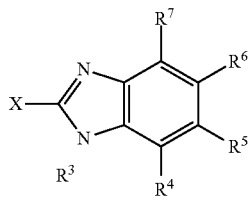

or a pharmaceutically acceptable salt or prodrug thereof, wherein X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl; $R^3$ is hydrogen, substituted or unsubstituted alkyl, and substituted or unsubstituted aryl; and $R^4$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Optionally, the compounds described herein are isotopically substituted with a stable isotope. The stable isotope can be, for example, deuterium, $^{13}C$, $^{15}N$, and/or $^{18}O$.

Also described herein is a composition including a compound as described herein and a pharmaceutically acceptable carrier.

Further described herein is a kit including a compound or composition as described herein.

Methods of treating or preventing a steroid receptor coactivator-related disease in a subject are also provided herein. A method of treating or preventing a steroid receptor coactivator-related disease in a subject includes administering to the subject an effective amount of a compound as described above. Optionally, the steroid receptor coactivator-related disease is cancer, a metabolic disorder, human immunodeficiency virus, a neurodegenerative disorder, or an inflammatory disease. Optionally, the steroid receptor coactivator is SRC-1, SRC-2, or SRC-3. The methods can further include administering a second compound or composition. Optionally, the second compound or composition is a chemotherapeutic agent.

Also described herein are methods of treating a metabolic disorder, human immunodeficiency virus, a neurodegenerative disorder, or an inflammatory disease in a subject. A method of treating a metabolic disorder, human immunodeficiency virus, a neurodegenerative disorder, or an inflammatory disease in a subject comprises administering to the subject an effective amount of a compound of the following formula:

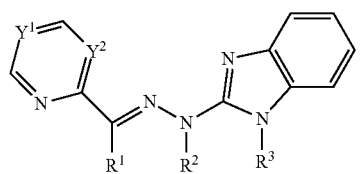

or a pharmaceutically acceptable salt or prodrug thereof, wherein $Y^1$ and $Y^2$ are each independently selected from CH or N; and $R^1$, $R^2$, and $R^3$ are each independently selected from hydrogen, substituted or unsubstituted alkyl, or substituted or unsubstituted aryl. In this method, at least one of $Y^1$ and $Y^2$ is N. Optionally, the compound is selected from the group consisting of:

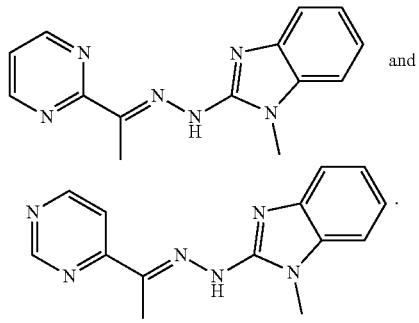

and

Methods of regulating a steroid receptor coactivator protein in a cell are also provided herein. A method of regulating a steroid receptor coactivator protein in a cell includes contacting a cell with an effective amount of a compound as described herein. The steroid receptor coactivator protein can optionally be SRC-1, SRC-2, or SRC-3. Optionally, the contacting is performed in vitro or in vivo.

Further described herein are compounds of the following formula:

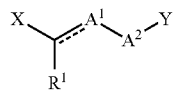

or a pharmaceutically acceptable salt or prodrug thereof, wherein === is a single bond or a double bond; X and Y are each independently selected from the group consisting of substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, substituted or unsubstituted alkynyl, substituted or unsubstituted cycloalkyl, and substituted or unsubstituted heterocycloalkyl; $A^1$ is B, CR, CRR', N, NR, O, or S; $A^2$ is BR, CRR', NR, O, or S; R and R' are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl; and $R^1$ is hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl, wherein if X is pyridine, === is a double bond, $A^1$ is N, $A^2$ is NH, and $R^1$ is methyl, then Y is not unsubstituted benzimidazole or N-methylbenzimidazole.

Also described herein are methods of using the compound shown above for treating or preventing a steroid receptor coactivator-related disease in a subject. The method of treating or preventing a steroid receptor coactivator-related disease in a subject comprises administering to the subject an effective amount of the compound.

The details of one or more embodiments are set forth in the drawings and the description below. Other features, objects, and advantages will be apparent from the description and drawings, and from the claims.

DESCRIPTION OF DRAWINGS

In FIG. 1, the first histogram bar in each set represents pBIND; the second histogram bar in each set represents SRC-1; the third histogram bar in each set represents SRC-2; and the fourth histogram bar in each set represents SRC-3.

In FIG. 2, the left histogram bar in each set represents pBIND and the right histogram bar in each set represents pBIND-SRC3.

DETAILED DESCRIPTION

Figure 1:
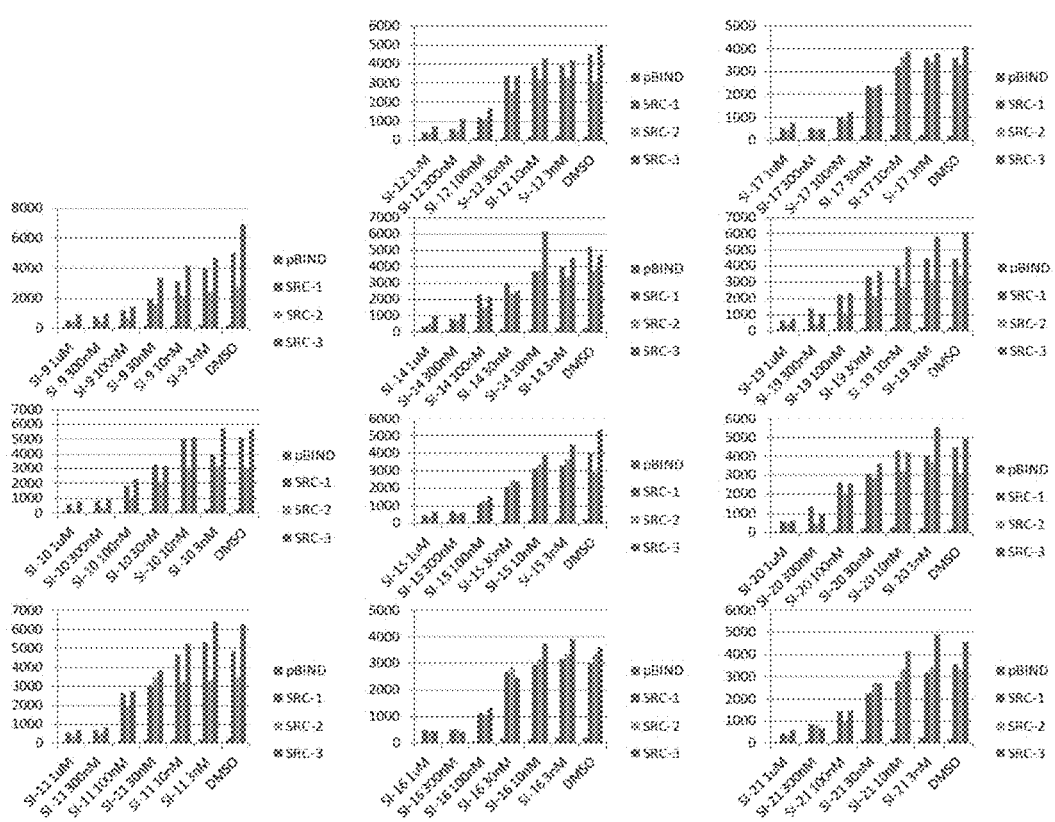
FIG. 1 shows results for a series of compounds that were tested for their effects on SRC-1, SRC-2 and SRC-3 intrinsic transcriptional activity. Luciferase assays were performed in HeLa cells transiently transfected with the reporter vector pG5-LUC in combination with expression vectors for pBIND and pBIND-SRC-3 before incubation with the compound for 24 hours.

Described herein are steroid receptor coactivator (SRC) modulators and methods for their use. Specifically, the small molecules described herein are modulators of one or more of the SRC family protein members, including SRC-1, SRC-2, and/or SRC-3. The compounds and methods described herein are useful for treating cancer, metabolic disorders, human immunodeficiency virus, neurodegenerative disorders, inflammatory diseases, and other SRC-related diseases.

I. Compounds

In some cases, the SRC modulators described herein are represented by the following formula:

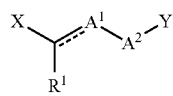

and pharmaceutically acceptable salts and prodrugs thereof.

In the formula shown above, === is a single bond or a double bond.

Also, in the formula shown above, X and Y are each independently selected from the group consisting of substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, substituted or unsubstituted alkynyl, substituted or unsubstituted cycloalkyl, and substituted or unsubstituted heterocycloalkyl. Optionally, X or Y is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Additionally, in the formula shown above, $A^1$ is B, CR, CRR', N, NR, O, or S, as appropriate based on whether === is a single bond or double bond. For example, when === is a double bond, $A^1$ can be CR or N. When === is a single bond, $A^1$ can be CRR', NR, O, or S. R and R' are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Further, in the formula shown above, $A^2$ is BR, CRR', NR, O, or S. R and R' are as defined above for $A^1$.

Optionally, === is a double bond, $A^1$ is N, and $A^2$ is NH or O.

Also, in the formula shown above, $R^1$ can be hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

In some embodiments, if X is pyridine, === is a double bond, $A^1$ is N, $A^2$ is NH, and $R^1$ is methyl, then Y is not unsubstituted benzimidazole or N-methyl-benzimidazole.

Exemplary classes of SRC modulators according to the structure shown above are provided below as Formula I, Formula II, Formula III, Formula IV, Formula V, Formula VI, Formula VII, Formula VIII, and Formula IX.

The SRC modulators described above and in subsequent formulas throughout this application are depicted in the E-conformation. However, the SRC modulators found throughout this application can be in either the E-conformation or in the Z-conformation, as shown below, regardless of the exemplary depiction in the application.

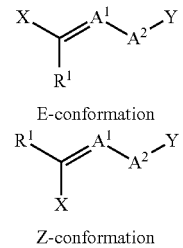

A class of SRC modulators described herein is represented by Formula I:

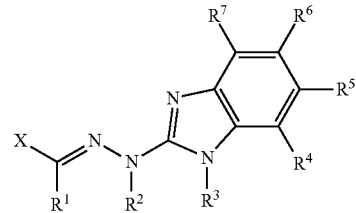

and pharmaceutically acceptable salts or prodrugs thereof.

In Formula I, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula I, $R^1$, $R^4$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Additionally in Formula I, $R^2$ and $R^3$ are each independently selected from hydrogen, substituted or unsubstituted alkyl, and substituted or unsubstituted aryl. Optionally, $R^2$ and $R^3$ are each selected from hydrogen and methyl.

Optionally, in Formula I, $R^1$ and $R^2$ combine to form a substituted or unsubstituted heterocycloalkyl, a substituted or unsubstituted heterocycloalkenyl, or a substituted or unsubstituted heteroaryl.

In some examples of Formula I, when X is a pyridine or a pyrimidine, the pyridine or the pyrimidine is substituted (i.e., the pyridine or pyrimidine contains at least one non-hydrogen substituent). In some examples of Formula I, when X is a pyridine or a pyrimidine, at least one of $R^4$, $R^5$, $R^6$, and $R^7$ is other than hydrogen. In some examples of Formula I, when X is pyridine or pyrimidine, $R^1$ is other than hydrogen, substituted or unsubstituted alkyl, substituted or unsubstituted aryl, substituted or unsubstituted heteroaryl, or substituted or unsubstituted cycloalkyl.

In some examples, Formula I is represented by Structure I-A:

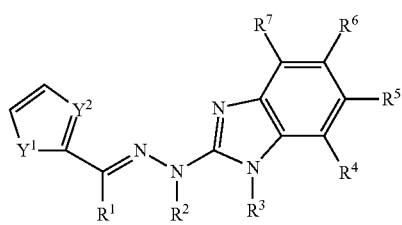

Structure I-A

In Structure I-A, $R^1$, $R^2$, $R^3$, $R^4$, $R^5$, $R^6$, and $R^7$ are as defined above for Formula I.

Also in Structure I-A, $Y^1$ is CRR, NR, O, or S.

Additionally in Structure I-A, $Y^2$ is CR or N.

When $Y^1$ and/or $Y^2$ is NR, CR, or CRR, each R can be hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl. Optionally, each R is hydrogen or substituted or unsubstituted alkyl (e.g., methyl).

In some examples of Structure I-A, $Y^1$ can be a heteroatom and $Y^2$ can be CH. For example, the compound of Structure I-A can be represented by Structure I-A1, Structure I-A2, or Structure I-A3:

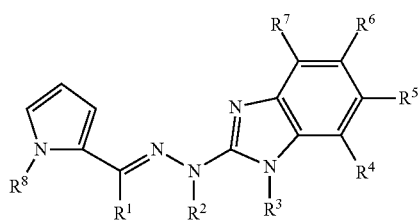

Structure I-A1

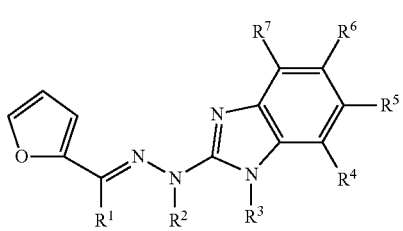

Structure I-A2

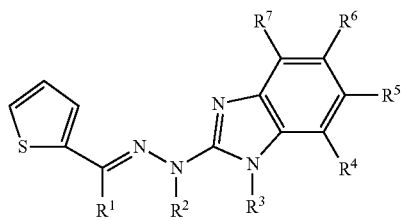

Structure I-A3

In Structure I-A1, Structure I-A2, and Structure I-A3, $R^1$, $R^2$, $R^3$, $R^4$, $R^5$, $R^6$, and $R^7$ are as defined above for Formula I. Also, in Structure I-A1, $R^8$ can be hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl.

In some examples of Structure I-A, $Y^1$ and $Y^2$ can both be heteroatoms. For example, the compound of Structure I-A can be represented by Structure I-A4, Structure I-A5, or Structure I-A6:

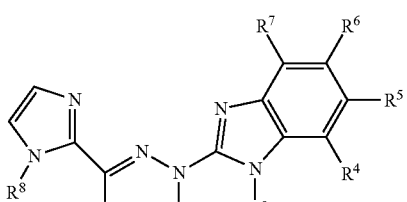

Structure I-A4

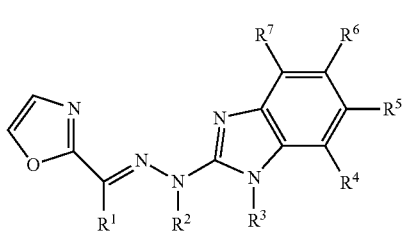

Structure I-A5

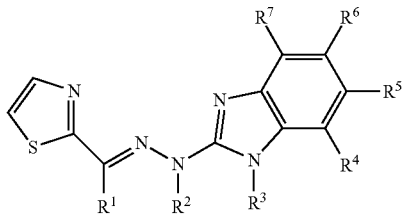

Structure I-A6

In Structure I-A4, Structure I-A5, and Structure I-A6, $R^1$, $R^2$, $R^3$, $R^4$, $R^5$, $R^6$, and $R^7$ are as defined above for Formula I. Also, in Structure I-A4, $R^8$ can be hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl.

Examples of Structure I-A include the following compounds:

Compound SI-3
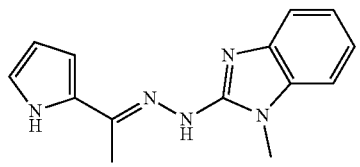

Compound SI-4
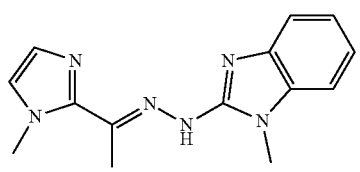

Compound SI-5
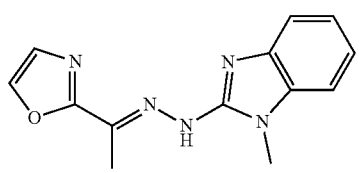

Compound SI-6
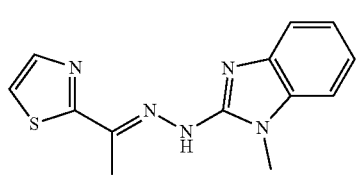

Compound SI-7
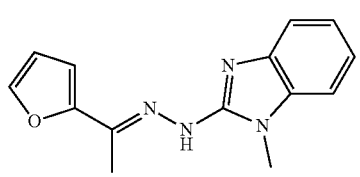

Compound SI-8
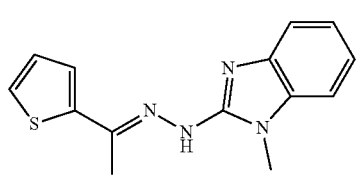

In some examples, Formula I is represented by Structure I-B:

Structure I-B
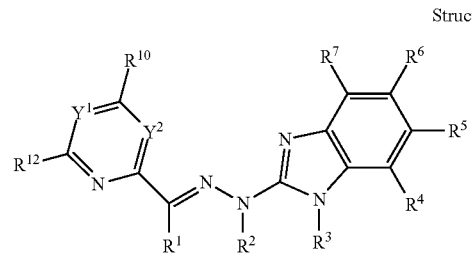

In Structure I-B, $R^1$, $R^2$, $R^3$, $R^4$, $R^5$, $R^6$, and $R^7$ are as defined above for Formula I.

Also in Structure I-B, $Y^1$ and $Y^2$ are each independently selected from CR or N. R can be hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl. Optionally, R is hydrogen or halogen (e.g., bromo, chloro, fluoro, or iodo).

Additionally in Structure I-B, $R^{10}$ and $R^{12}$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl. Optionally, $R^{10}$ and $R^{12}$ are selected from hydrogen or halogen (e.g., bromo, chloro, fluoro, or iodo).

Further, in Structure I-B, at least one of $R^4$, $R^5$, $R^6$, $R^7$, $R^{10}$, $R^{12}$, and R (when $Y^1$ or $Y^2$ is CR) is other than hydrogen.

In some examples of Structure I-B, $Y^1$ and $Y^2$ can both be CH such that a pyridine is formed. For example, the compound of Structure I-B can be represented by Structure I-B1:

Structure I-B1
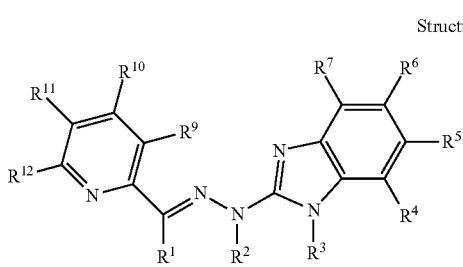

In Structure I-B1, $R^2$, $R^3$, $R^4$, $R^5$, $R^6$, $R^7$, $R^{10}$, and $R^{12}$ are as defined above for Structure I-B. $R^9$ and $R^{11}$ can each be independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

In some examples of Structure I-B, $Y^1$ or $Y^2$ can be N such that a pyrimidine is formed. For example, the compound of Structure I-B can be represented by Structure I-B2 or Structure I-B3:

Structure I-B2
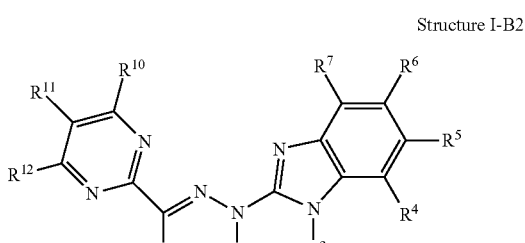

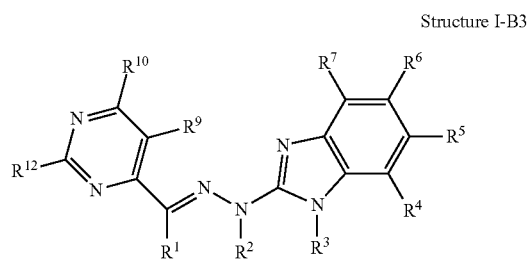

Structure I-B3

In Structure I-B2, $R^1$, $R^2$, $R^3$, $R^4$, $R^5$, $R^6$, $R^7$, $R^{10}$, $R^{11}$, and $R^{12}$ are as defined above for Structure I-B1. In Structure I-B3, $R^1$, $R^2$, $R^3$, $R^4$, $R^5$, $R^6$, $R^7$, $R^9$, $R^{10}$, and $R^{12}$ are as defined above for Structure I-B1.

Examples of Structure I-B include the following compounds:

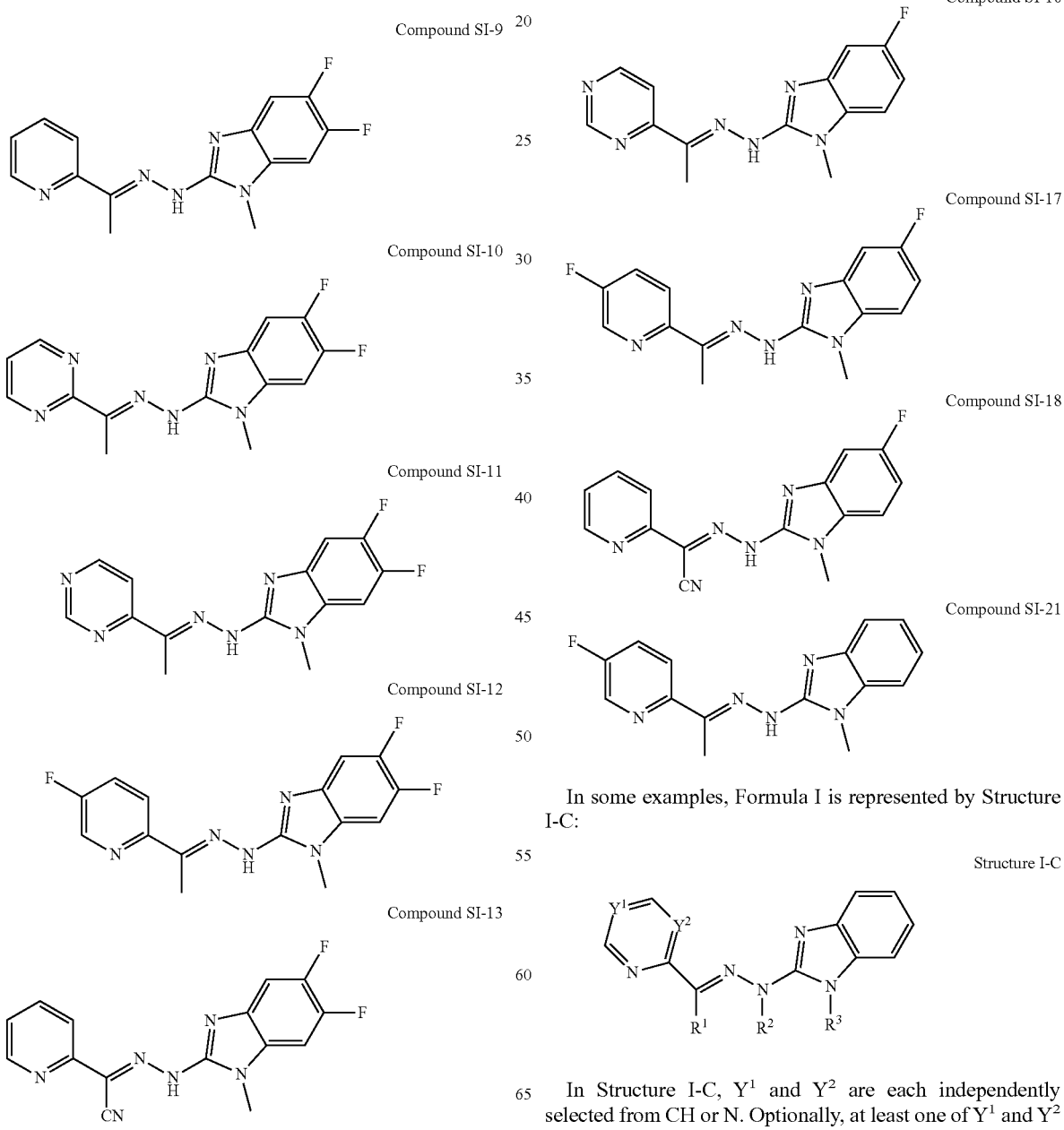

In some examples, Formula I is represented by Structure I-C:

Structure I-C

In Structure I-C, $Y^1$ and $Y^2$ are each independently selected from CH or N. Optionally, at least one of $Y^1$ and $Y^2$ is N.

Also in Structure I-C, $R^1$, $R^2$, and $R^3$ are each independently selected from hydrogen, substituted or unsubstituted alkyl, and substituted or unsubstituted aryl.

In some examples of Structure I-C, $Y^1$ and $Y^2$ can both be CH such that a pyridine is formed. For example, the compound of Structure I-C can be represented by Structure I-C1:

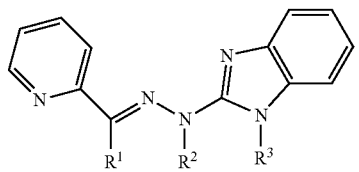

Structure I-C1

In Structure I-C1, $R^2$, and $R^3$ are as defined above for Structure I-C.

In some examples of Structure I-C, $Y^1$ or $Y^2$ can be N such that a pyrimidine is formed. For example, the compound of Structure I-C can be represented by Structure I-C2 or Structure I-C3:

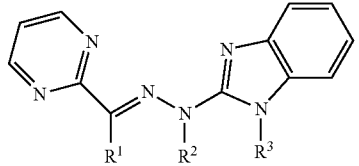

Structure I-C2

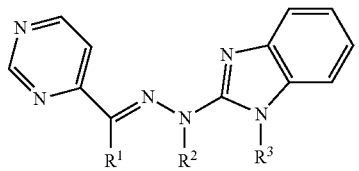

Structure I-C3

In Structure I-C2 and Structure I-C3, $R^2$, and $R^3$ are as defined above for Structure I-C.

Examples of Structure I-C include the following compounds:

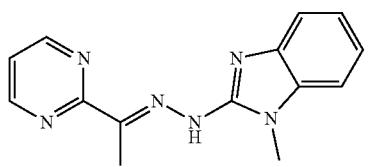

Compound SI-19

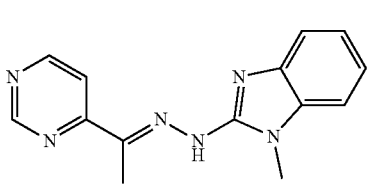

Compound SI-20

Further examples of Formula I includes the following compounds:

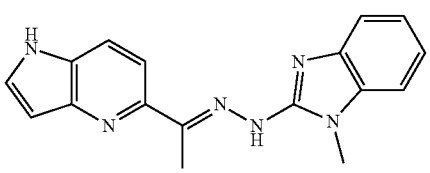

Compound 1

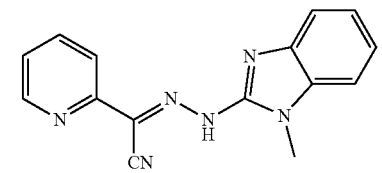

Compound SI-22

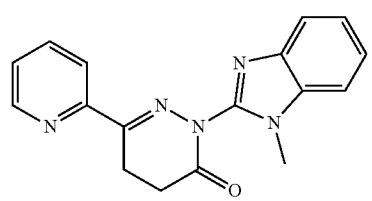

Compound SI-D-01

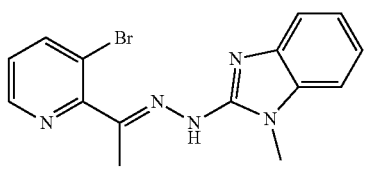

Compound SI-E-01P

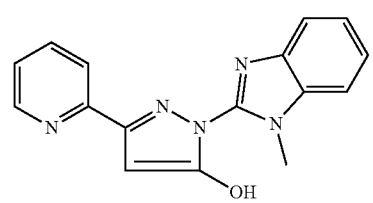

Compound SI-F-01

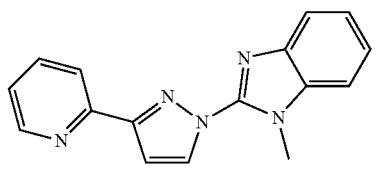

Compound SI-H-01

In some cases, the SRC modulators described herein may exist as tautomers. All tautomers are included within the scope of the compounds presented herein. For example, the SRC modulators according to Formula I can exist as tautomers as represented by Formula I(T), i.e., Formula I (Tautomer):

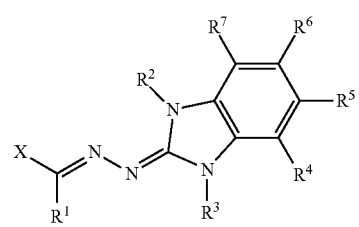

and pharmaceutically acceptable salts or prodrugs thereof.

In Formula I(T), X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula I(T), $R^4$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Additionally in Formula I(T), $R^2$ and $R^3$ are each independently selected from hydrogen, substituted or unsubstituted alkyl, and substituted or unsubstituted aryl. Optionally, $R^2$ and $R^3$ are each selected from hydrogen and methyl.

In some examples of Formula I(T), when X is a pyridine or a pyrimidine, the pyridine or the pyrimidine is substituted (i.e., the pyridine or pyrimidine contains at least one non-hydrogen substituent). In some examples of Formula I(T), when X is a pyridine or a pyrimidine, at least one of $R^4$, $R^5$, $R^6$, and $R^7$ is other than hydrogen. In some examples of Formula I(T), when X is pyridine or pyrimidine, $R^1$ is other than hydrogen, substituted or unsubstituted alkyl, substituted or unsubstituted aryl, substituted or unsubstituted heteroaryl, or substituted or unsubstituted cycloalkyl.

In some examples, Formula I(T) is represented by Structure I-A(T):

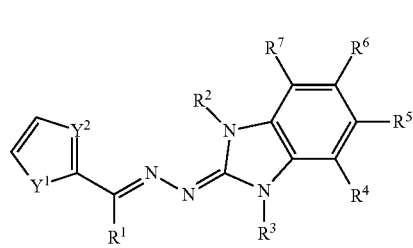

Structure I-A(T)

In Structure I-A(T), $R^1$, $R^2$, $R^3$, $R^4$, $R^5$, $R^6$, and $R^7$ are as defined above for Formula I(T).

Also in Structure I-A(T), $Y^1$ is CRR, NR, O, or S.

Additionally in Structure I-A(T), $Y^2$ is CR or N.

When $Y^1$ and/or $Y^2$ is NR, CR, or CRR, each R can be hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl. Optionally, each R is hydrogen or substituted or unsubstituted alkyl (e.g., methyl).

In some examples of Structure I-A(T), $Y^1$ can be a heteroatom and $Y^2$ can be CH. For example, the compound of Structure I-A(T) can be represented by Structure I-A1(T), Structure I-A2(T), or Structure I-A3(T):

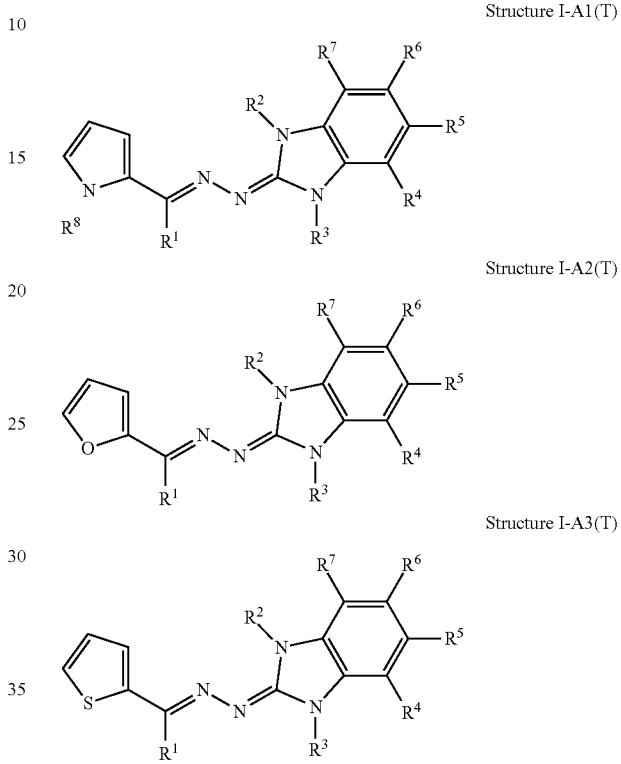

In Structure I-A1(T), Structure I-A2(T), and Structure I-A3(T), $R^1$, $R^2$, $R^3$, $R^4$, $R^5$, $R^6$, and $R^7$ are as defined above for Formula I(T). Also, in Structure I-A1(T), $R^8$ can be hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl.

In some examples of Structure I-A(T), $Y^1$ and $Y^2$ can both be heteroatoms. For example, the compound of Structure I-A(T) can be represented by Structure I-A4(T), Structure I-A5(T), or Structure I-A6(T):

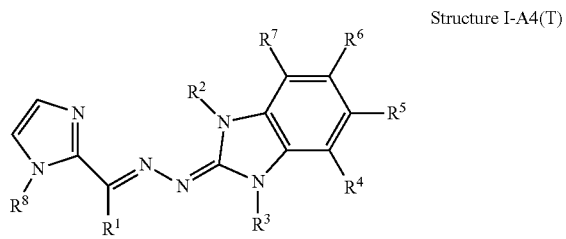

Structure I-A4(T)

Structure I-A5(T)

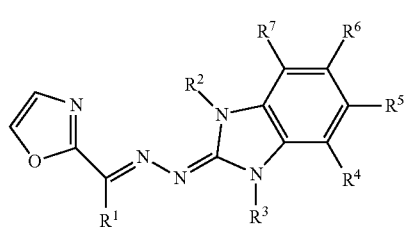

Structure I-A6(T)

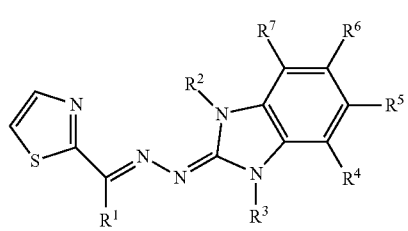

In Structure I-A4(T), Structure I-A5(T), and Structure I-A6(T), $R^1$, $R^2$, $R^3$, $R^4$, $R^5$, $R^6$, and $R^7$ are as defined above for Formula I(T). Also, in Structure I-A4(T), $R^8$ can be hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl.

Examples of Structure I-A(T) include the following compounds:

Compound SI-3(T)

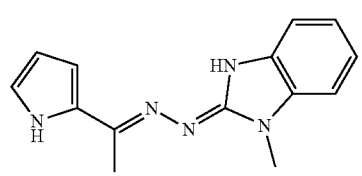

Compound SI-4(T)

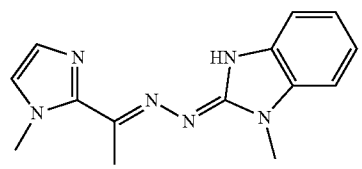

Compound SI-5(T)

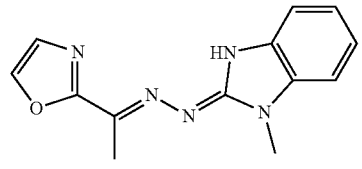

Compound SI-6(T)

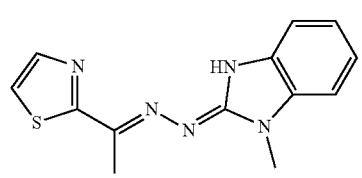

Compound SI-7(T)

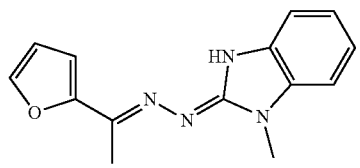

Compound SI-8(T)

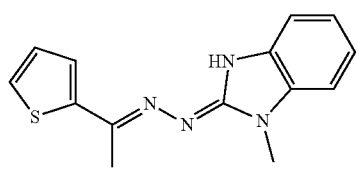

In some examples, Formula I(T) is represented by Structure I-B(T):

Structure I-B(T)

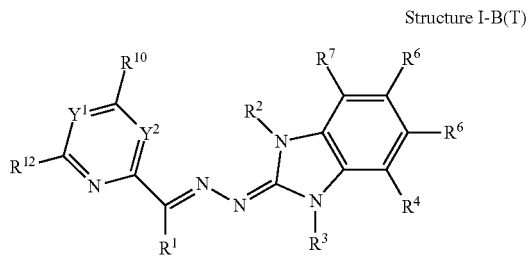

In Structure I-B(T), $R^1$, $R^2$, $R^3$, $R^4$, $R^5$, $R^6$, and $R^7$ are as defined above for Formula I(T).

Also in Structure I-B(T), $Y^1$ and $Y^2$ are each independently selected from CR or N. R can be hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl. Optionally, R is hydrogen or halogen (e.g., bromo, chloro, fluoro, or iodo).

Additionally in Structure I-B(T), $R^{10}$ and $R^{12}$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl. Optionally, $R^{10}$ and $R^{12}$ are selected from hydrogen or halogen (e.g., bromo, chloro, fluoro, or iodo).

Further, in Structure I-B(T), at least one of $R^4$, $R^5$, $R^6$, $R^7$, $R^{10}$, $R^{12}$, and R (when $Y^1$ or $Y^2$ is CR) is other than hydrogen.

In some examples of Structure I-B(T), $Y^1$ and $Y^2$ can both be CH such that a pyridine is formed. For example, the compound of Structure I-B(T) can be represented by Structure I-B1(T):

Structure I-B1(T)

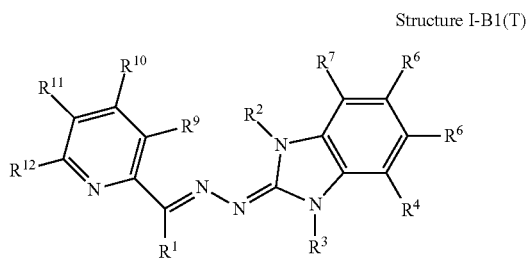

In Structure I-B1(T), $R^2$, $R^3$, $R^4$, $R^5$, $R^6$, $R^7$, $R^{10}$, and $R^{12}$ are as defined above for Structure I-B(T). $R^9$ and $R^{11}$ can each be independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

In some examples of Structure I-B(T), $Y^1$ or $Y^2$ can be N such that a pyrimidine is formed. For example, the compound of Structure I-B(T) can be represented by Structure I-B2(T) or Structure I-B3(T):

Structure I-B2(T)

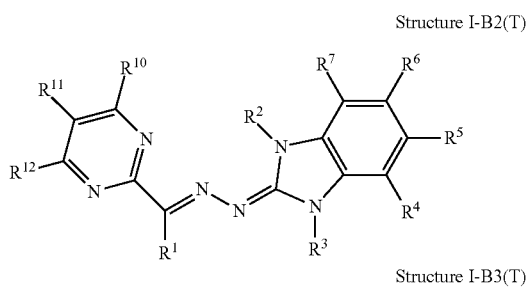

Structure I-B3(T)

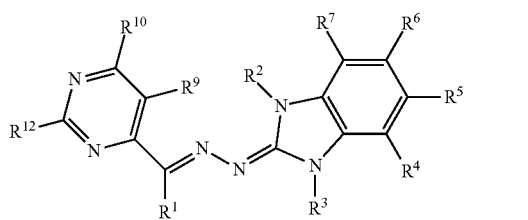

In Structure I-B2 (T), $R^1$, $R^2$, $R^3$, $R^4$, $R^5$, $R^6$, $R^7$, $R^9$, $R^{10}$, and $R^{12}$ are as defined above for Structure I-B1(T). In Structure I-B3(T), $R^1$, $R^2$, $R^3$, $R^4$, $R^5$, $R^6$, $R^7$, $R^9$, $R^{10}$, and $R^{12}$ are as defined above for Structure I-B1(T).

Examples of Structure I-B(T) include the following compounds:

Compound SI-9(T)

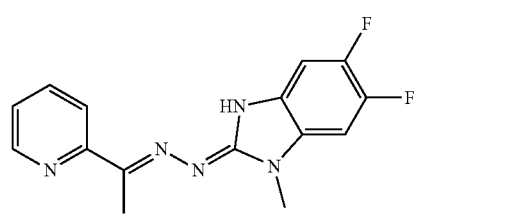

Compound SI-10(T)

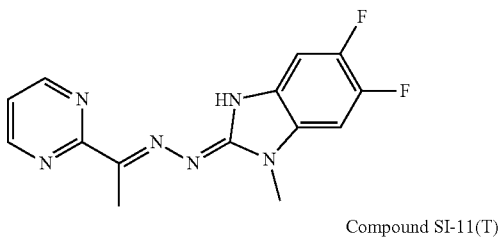

Compound SI-11(T)

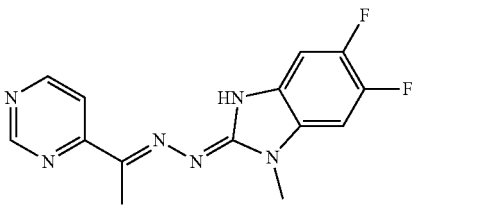

Compound SI-12(T)

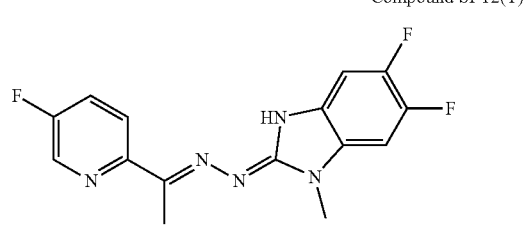

Compound SI-13(T)

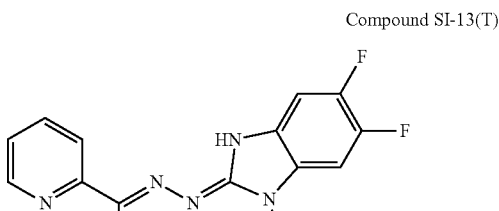

Compound SI-14(T)

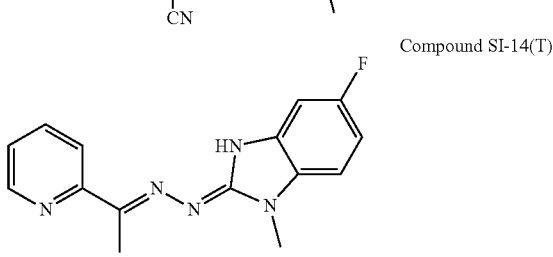

Compound SI-15(T)

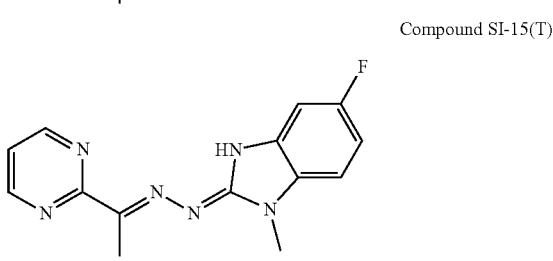

Compound SI-16(T)

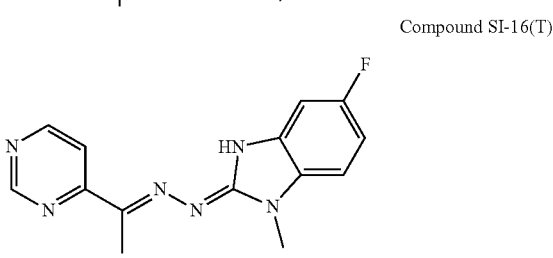

-continued

Compound SI-17(T)

Compound SI-18(T)

Compound SI-21(T)

Compound SI-2-NMe

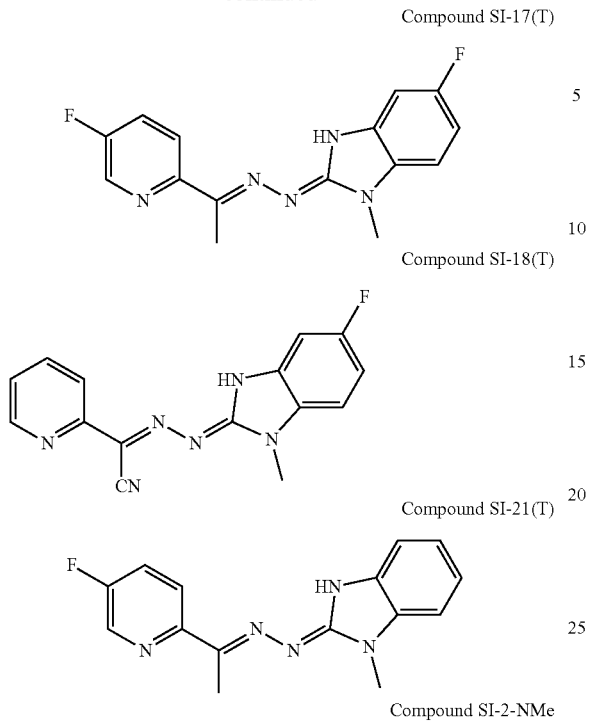

In some examples, Formula I(T) is represented by Structure I-C(T):

Structure I-C(T)

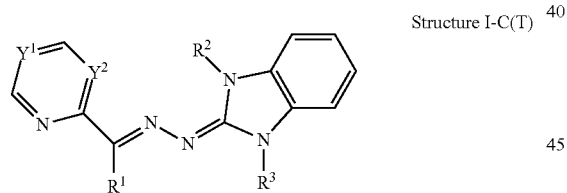

In Structure I-C(T), $Y^1$ and $Y^2$ are each independently selected from CH or N. Optionally, at least one of $Y^1$ and $Y^2$ is N.

Also in Structure I-C(T), $R^1$, $R^2$, and $R^3$ are each independently selected from hydrogen, substituted or unsubstituted alkyl, and substituted or unsubstituted aryl.

In some examples of Structure I-C(T), $Y^1$ and $Y^2$ can both be CH such that a pyridine is formed. For example, the compound of Structure I-C(T) can be represented by Structure I-C1(T):

Structure I-C1(T)

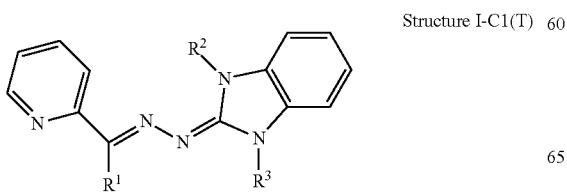

In Structure I-C1(T), $R^1$, $R^2$, and $R^3$ are as defined above for Structure I-C(T).

In some examples of Structure I-C(T), $Y^1$ or $Y^2$ can be N such that a pyrimidine is formed. For example, the compound of Structure I-C(T) can be represented by Structure I-C2(T) or Structure I-C3(T):

Structure I-C2(T)

Structure I-C3(T)

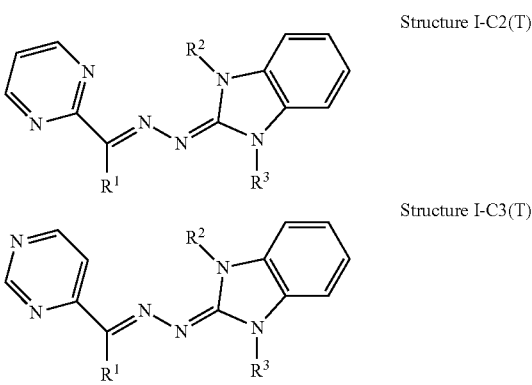

In Structure I-C2(T) and Structure I-C3(T), $R^1$, $R^2$, and $R^3$ are as defined above for Structure I-C(T).

Examples of Structure I-C(T) include the following compounds:

Compound SI-19(T)

Compound SI-20(T)

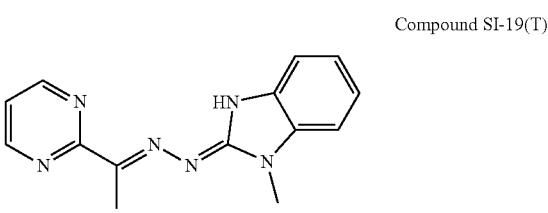

Further examples of Formula I(T) includes the following compounds:

Compound 1(T)

Compound SI-22(T)

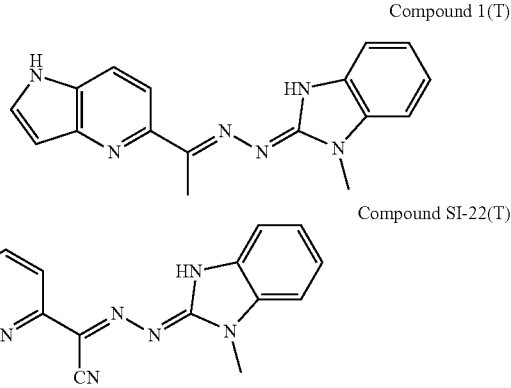

Optionally, the SRC modulators described herein may exist as mixtures of tautomeric forms. For example, the SRC modulators described herein can include a mixture of compounds according to Formula I and compounds according to Formula I(T). In some examples, the SRC modulators described herein can exist in a tautomeric mixture wherein the compound according to Formula I(T) is the major tautomer present and the compound according to Formula I is the minor tautomer present. As used herein, major tautomer present refers to the tautomer present in an amount greater than 50% by weight of the SRC modulators (e.g., 60% by weight or more, 70% by weight or more, 80% by weight or more, 90% by weight or more, or 95% by weight or more). As used herein, minor tautomer present refers to the tautomer present in an amount less than 50% by weight of the SRC modulators (e.g., 40% by weight or less, 30% by weight or less, 20% by weight or less, 10% by weight or less, or 5% by weight or less). In other examples, the SRC modulators described herein can exist in a tautomeric mixture wherein the compound according to Formula I is the major tautomer present and the compound according to Formula I(T) is the minor tautomer present.

Though not depicted herein, tautomeric forms and mixtures are contemplated for Formula II, Formula III, Formula V, Formula VII, Formula X, Formula XI, Formula XIII, and Formula XIV shown below.

A class of SRC modulators described herein is represented by Formula II:

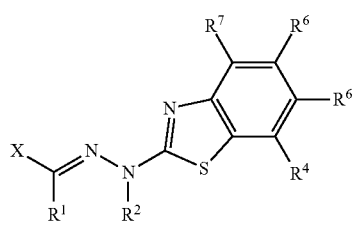

and pharmaceutically acceptable salts or prodrugs thereof.

In Formula II, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula II, $R^1$, $R^4$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Additionally in Formula II, $R^2$ is hydrogen, substituted or unsubstituted alkyl, or substituted or unsubstituted aryl. Optionally, $R^2$ is hydrogen or methyl.

Optionally, in Formula II, $R^1$ and $R^2$ combine to form a substituted or unsubstituted heterocycloalkyl, a substituted or unsubstituted heterocycloalkenyl, or a substituted or unsubstituted heteroaryl.

Examples of Formula II include the following compounds:

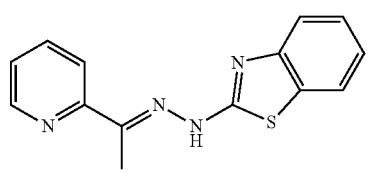

Compound 2

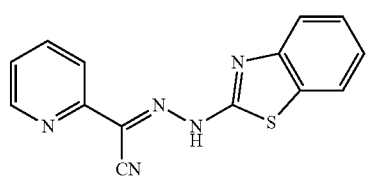

Compound 3

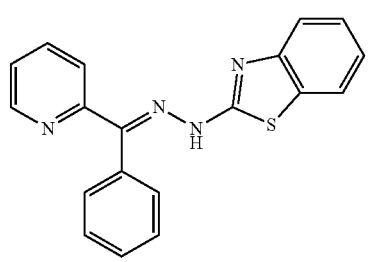

Compound 4

A class of SRC modulators described herein is represented by Formula III:

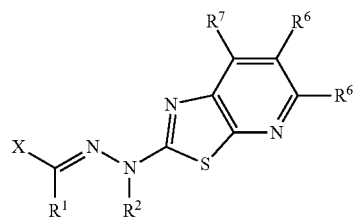

and pharmaceutically acceptable salts or prodrugs thereof.

In Formula III, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula III, $R^1$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Additionally in Formula III, $R^2$ is hydrogen, substituted or unsubstituted alkyl, or substituted or unsubstituted aryl. Optionally, $R^2$ is hydrogen or methyl.

Optionally, in Formula III, $R^1$ and $R^2$ combine to form a substituted or unsubstituted heterocycloalkyl, a substituted or unsubstituted heterocycloalkenyl, or a substituted or unsubstituted heteroaryl.

An example of Formula III includes the following compound:

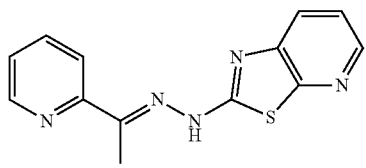

Compound 5

A class of SRC modulators described herein is represented by Formula IV:

X—C(R¹)=N—O—[thiazolopyridine with R⁵, R⁶, R⁷]

and pharmaceutically acceptable salts or prodrugs thereof.

In Formula IV, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula IV, $R^1$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

An example of Formula IV includes the following compound:

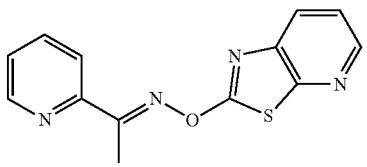

Compound 6

A class of SRC modulators described herein is represented by Formula V:

and pharmaceutically acceptable salts or prodrugs thereof.

In Formula V, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula V, $R^1$, $R^5$, and $R^6$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Additionally in Formula V, $R^2$, $R^3$, and $R^4$ are each independently selected from hydrogen, substituted or unsubstituted alkyl, and substituted or unsubstituted aryl. Optionally, $R^2$, $R^3$, and $R^4$ are each selected from hydrogen and methyl.

Optionally, in Formula V, $R^1$ and $R^2$ combine to form a substituted or unsubstituted heterocycloalkyl, a substituted or unsubstituted heterocycloalkenyl, or a substituted or unsubstituted heteroaryl.

A class of SRC modulators described herein is represented by Formula VI:

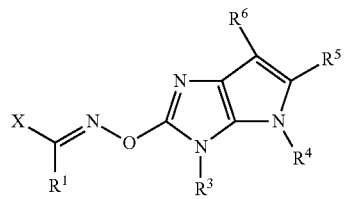

and pharmaceutically acceptable salts or prodrugs thereof.

In Formula VI, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula VI, $R^1$, $R^5$, and $R^6$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Additionally in Formula VI, $R^3$ and $R^4$ are each independently selected from hydrogen, substituted or unsubstituted alkyl, and substituted or unsubstituted aryl. Optionally, $R^3$ and $R^4$ are each selected from hydrogen and methyl.

An example of Formula VI includes the following compound:

Compound 7

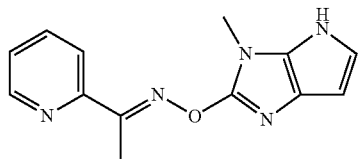

A class of SRC modulators described herein is represented by Formula VII:

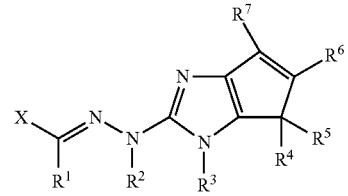

and pharmaceutically acceptable salts or prodrugs thereof.

In Formula VII, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula VII, $R^1$, $R^4$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Additionally in Formula VII, $R^2$ and $R^3$ are each independently selected from hydrogen, substituted or unsubstituted alkyl, and substituted or unsubstituted aryl. Optionally, $R^2$ and $R^3$ are each selected from hydrogen and methyl.

Optionally, in Formula VII, $R^1$ and $R^2$ combine to form a substituted or unsubstituted heterocycloalkyl, a substituted or unsubstituted heterocycloalkenyl, or a substituted or unsubstituted heteroaryl.

A class of SRC modulators described herein is represented by Formula VIII:

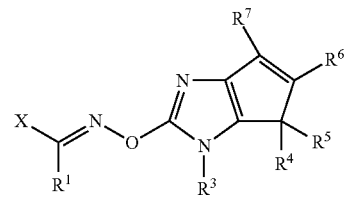

and pharmaceutically acceptable salts or prodrugs thereof.

In Formula VIII, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula VIII, $R^1$, $R^4$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Additionally in Formula VIII, $R^3$ is hydrogen, substituted or unsubstituted alkyl, or substituted or unsubstituted aryl. Optionally, $R^3$ is hydrogen or methyl.

An example of Formula VIII includes the following compound:

Compound 8

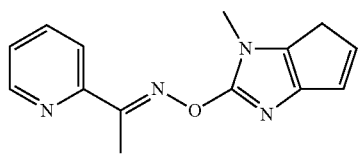

A class of SRC modulators described herein is represented by Formula IX:

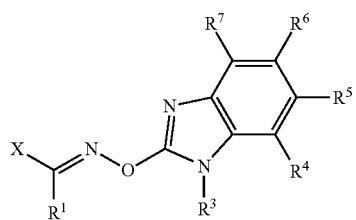

and pharmaceutically acceptable salts or prodrugs thereof.

In Formula IX, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula IX, $R^1$, $R^4$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

Additionally in Formula IX, $R^3$ is hydrogen, substituted or unsubstituted alkyl, or substituted or unsubstituted aryl. Optionally, $R^3$ is hydrogen or methyl.

An example of Formula IX includes the following compound:

Compound SI-B-01

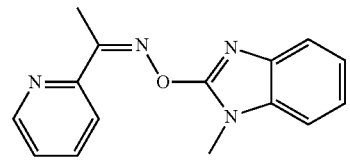

Further exemplary classes of SRC modulators are provided below as Formula X, Formula XI, Formula XII, Formula XIII, and Formula XIV.

A class of SRC modulators described herein is represented by Formula X:

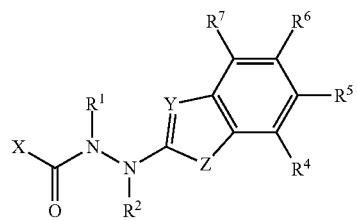

and pharmaceutically acceptable salts or prodrugs thereof.

In Formula X, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula X, Y is selected from the group consisting of N, P, and B.

Additionally in Formula X, Z is selected from the group consisting of $NR^3$, $PR^3$, $BR^3$, O, and S. $R^3$ is hydrogen, substituted or unsubstituted alkyl, and substituted or unsubstituted aryl. Optionally, $R^3$ is hydrogen or methyl.

Additionally in Formula X, $R^1$ and $R^2$ are each independently selected from hydrogen, substituted or unsubstituted alkyl, and substituted or unsubstituted aryl. Optionally, $R^1$ and $R^2$ are each selected from hydrogen and methyl.

Also in Formula X, $R^4$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

In some examples, Formula X is represented by Structure X-A:

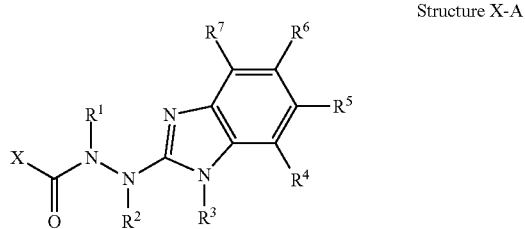

Structure X-A

In Structure X-A, X, $R^1$, $R^2$, $R^3$, $R^4$, $R^5$, $R^6$, and $R^7$ are as defined above for Formula X.

An example of Formula X includes the following compound:

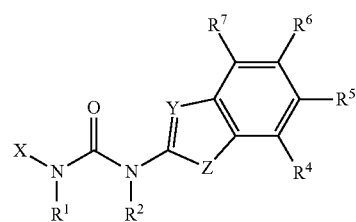

Compound SI-C-01

A class of SRC modulators described herein is represented by Formula XI:

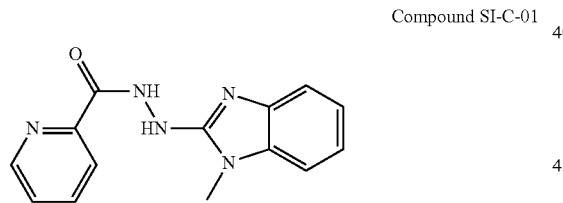

and pharmaceutically acceptable salts or prodrugs thereof.

In Formula XI, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula XI, Y is selected from the group consisting of N, P, and B.

Additionally in Formula XI, Z is selected from the group consisting of $NR^3$, $PR^3$, $BR^3$, O, and S. $R^3$ is hydrogen, substituted or unsubstituted alkyl, and substituted or unsubstituted aryl. Optionally, $R^3$ is hydrogen or methyl.

In Formula XI, $R^1$ and $R^2$ are each independently selected from hydrogen, substituted or unsubstituted alkyl, and substituted or unsubstituted aryl. Optionally, $R^1$ and $R^2$ are each selected from hydrogen and methyl.

Also in Formula XI, $R^4$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

In some examples, Formula XI is represented by Structure XI-A:

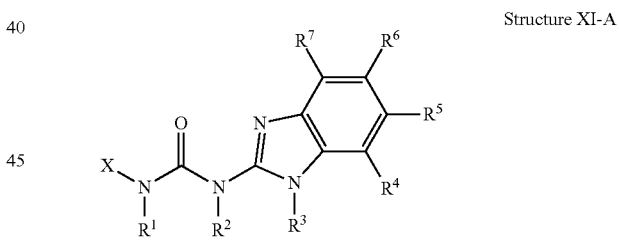

Structure XI-A

In Structure XI-A, X, $R^1$, $R^2$, $R^3$, $R^4$, $R^5$, $R^6$, and $R^7$ are as defined above for Formula XI.

An example of Formula XI includes the following compound:

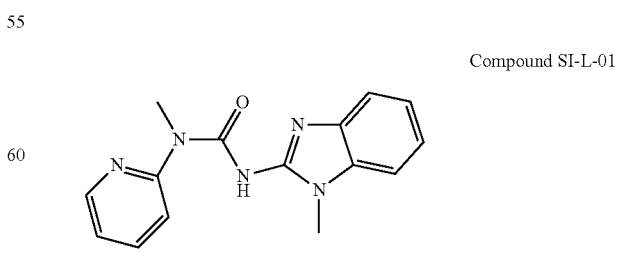

Compound SI-L-01

A class of SRC modulators described herein is represented by Formula XII:

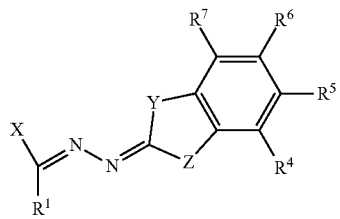

and pharmaceutically acceptable salts or prodrugs thereof.

In Formula XII, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula XII, Y is selected from the group consisting of $NR^2$, $PR^2$, $BR^2$, O, and S. $R^2$ is hydrogen, substituted or unsubstituted alkyl, or substituted or unsubstituted aryl. Optionally, $R^2$ is hydrogen or methyl.

Additionally in Formula XII, Z is selected from the group consisting of $NR^3$, $PR^3$, $BR^3$, O, and S. $R^3$ is hydrogen, substituted or unsubstituted alkyl, or substituted or unsubstituted aryl. Optionally, $R^3$ is hydrogen or methyl.

Also in Formula XII, $R^1$, $R^4$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

In some examples, Formula XII is represented by Structure XII-A:

Structure XII-A

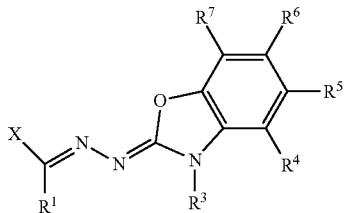

In Structure XII-A, X, $R^1$, $R^3$, $R^4$, $R^5$, $R^6$, and $R^7$ are as defined above for Formula XII.

An example of Formula XII includes the following compound:

Compound 9

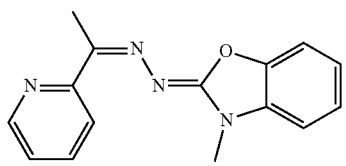

A class of SRC modulators described herein is represented by Formula XIII:

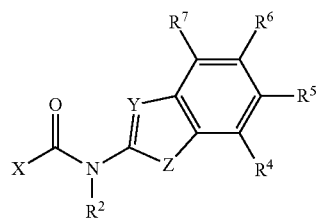

and pharmaceutically acceptable salts or prodrugs thereof.

In Formula XIII, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, or substituted or unsubstituted cyclopentaimidazole.

Also in Formula XIII, Y is selected from the group consisting of N, P, and B.

Additionally in Formula XIII, Z is selected from the group consisting of $NR^3$, $PR^3$, $BR^3$, O, and S. $R^3$ is hydrogen, substituted or unsubstituted alkyl, and substituted or unsubstituted aryl. Optionally, $R^3$ is hydrogen or methyl.

Also in Formula XIII, $R^2$ is selected from hydrogen, substituted or unsubstituted alkyl, and substituted or unsubstituted aryl. Optionally, $R^2$ is hydrogen or methyl.

Additionally in Formula XIII, $R^4$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

In some examples, Formula XIII is represented by Structure XIII-A:

Structure XIII-A

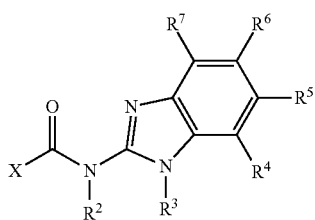

In Structure XIII-A, X, $R^2$, $R^3$, $R^4$, $R^5$, $R^6$, and $R^7$ are as defined above for Formula XIII An example of Formula XIII includes the following compound:

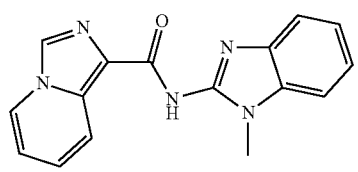

Compound 10

A class of SRC modulators described herein is represented by Formula XIV:

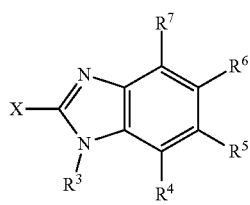

and pharmaceutically acceptable salts or prodrugs thereof.

In Formula XIV, X is a substituted or unsubstituted heterocycloalkyl, substituted or unsubstituted heterocycloalkenyl, substituted or unsubstituted heterocycloalkynyl, substituted or unsubstituted heteroaryl, substituted or unsubstituted aryl, substituted or unsubstituted alkyl, substituted or unsubstituted alkenyl, or substituted or unsubstituted alkynyl. Optionally, X is substituted or unsubstituted pyrrole, substituted or unsubstituted imidazole, substituted or unsubstituted thiazole, substituted or unsubstituted benzothiazole, substituted or unsubstituted thiophene, substituted or unsubstituted oxazole, substituted or unsubstituted furan, substituted or unsubstituted pyridine, substituted or unsubstituted pyrimidine, substituted or unsubstituted pyrazine, substituted or unsubstituted thiazolopyridine, substituted or unsubstituted imidazopyridine, substituted or unsubstituted pyrroloimidazole, substituted or unsubstituted cyclopentaimidazole, substituted or unsubstituted pyridopyridazinone, substituted or unsubstituted pyridotriazepine, substituted or unsubstituted naphthyridine, substituted or unsubstituted pyridopyrimidine, substituted or unsubstituted pyridooxazepine, substituted or unsubstituted pyridodiazepine, or substituted or unsubstituted pyridoazepine.

Also in Formula XIV, Y is selected from the group consisting of N, P, and B.

Additionally in Formula XIV, Z is selected from the group consisting of $NR^3$, $PR^3$, $BR^3$, O, and S. $R^3$ is hydrogen, substituted or unsubstituted alkyl, and substituted or unsubstituted aryl. Optionally, $R^3$ is hydrogen or methyl.

Additionally in Formula XIV, $R^4$, $R^5$, $R^6$, and $R^7$ are each independently selected from hydrogen, halogen (e.g., bromo, chloro, fluoro, or iodo), cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl.

In some examples, Formula XIV is represented by Structure XIV-A:

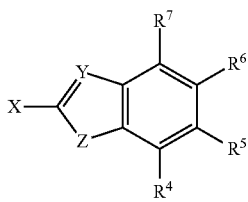

Structure XIV-A

In Structure XIV-A, X, $R^3$, $R^4$, $R^5$, $R^6$, and $R^7$ are as defined above for Formula XIV.

Examples of Formula XIV include the following compounds:

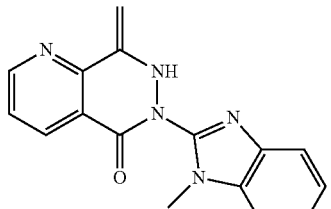

Compound SI-I-01

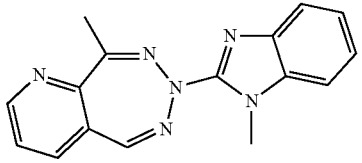

Compound SI-K-01

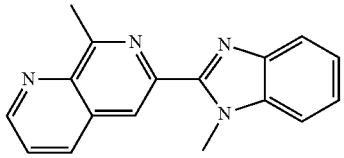

Compound 11

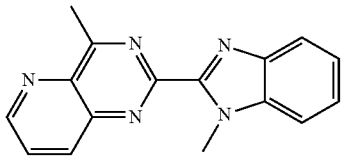

Compound 12

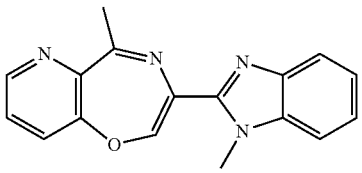

Compound 13

Compound 14

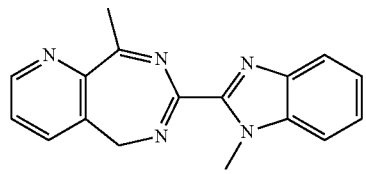

Compound 15

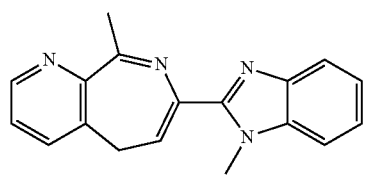

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{20}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_5$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline. The aryl and heteroaryl molecules can be attached at any position on the ring, unless otherwise noted.

The term alkoxy as used herein is an alkyl group bound through a single, terminal ether linkage. The term aryloxy as used herein is an aryl group bound through a single, terminal ether linkage. Likewise, the terms alkenyloxy, alkynyloxy, heteroalkyloxy, heteroalkenyloxy, heteroalkynyloxy, heteroaryloxy, cycloalkyloxy, and heterocycloalkyloxy as used herein are an alkenyloxy, alkynyloxy, heteroalkyloxy, heteroalkenyloxy, heteroalkynyloxy, heteroaryloxy, cycloalkyloxy, and heterocycloalkyloxy group, respectively, bound through a single, terminal ether linkage.

The term hydroxy as used herein is represented by the formula —OH.

The terms amine or amino as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The alkoxy, aryloxy, amino, alkyl, alkenyl, alkynyl, aryl, heteroalkyl, heteroalkenyl, heteroalkynyl, heteroaryl, cycloalkyl, or heterocycloalkyl molecules used herein can be substituted or unsubstituted. As used herein, the term substituted includes the addition of an alkoxy, aryloxy, amino, alkyl, alkenyl, alkynyl, aryl, heteroalkyl, heteroalkenyl, heteroalkynyl, heteroaryl, cycloalkyl, or heterocycloalkyl group to a position attached to the main chain of the alkoxy, aryloxy, amino, alkyl, alkenyl, alkynyl, aryl, heteroalkyl, heteroalkenyl, heteroalkynyl, heteroaryl, cycloalkyl, or heterocycloalkyl, e.g., the replacement of a hydrogen by one of these molecules. Examples of substitution groups include, but are not limited to, hydroxy, halogen (e.g., F, Br, Cl, or I), and carboxyl groups. Conversely, as used herein, the term unsubstituted indicates the alkoxy, aryloxy, amino, alkyl, alkenyl, alkynyl, aryl, heteroalkyl, heteroalkenyl, heteroalkynyl, heteroaryl, cycloalkyl, or heterocycloalkyl has a full complement of hydrogens, i.e., commensurate with its saturation level, with no substitutions, e.g., linear decane (—$(CH_2)_9$—$CH_3$).

II. Methods of Making the Compounds

The compounds described herein can be prepared in a variety of ways. The compounds can be synthesized using various synthetic methods. At least some of these methods are known in the art of synthetic organic chemistry. The compounds described herein can be prepared from readily available starting materials. Optimum reaction conditions can vary with the particular reactants or solvent used, but such conditions can be determined by one skilled in the art by routine optimization procedures.

Variations on Formula I, Formula II, Formula III, Formula IV, Formula V, Formula VI, Formula VII, Formula VIII, Formula IX, Formula X, Formula XI, Formula XII, Formula XIII, and Formula XIV, and tautomers thereof, include the addition, subtraction, or movement of the various constituents as described for each compound. Similarly, when one or more chiral centers are present in a molecule, all possible chiral variants are included. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts, Greene's Protective Groups in Organic Synthesis, 5th. Ed., Wiley & Sons, 2014, which is incorporated herein by reference in its entirety.

The compounds described herein can optionally be isotopically substituted. For example, the compounds described herein can be substituted with stable or nonradioactive isotopes, such as deuterium, $^{13}C$, $^{15}N$, and/or $^{18}O$. Incorporation of a heavy atom, such as substitution of deuterium for hydrogen, can give rise to an isotope effect that could alter the pharmacokinetics of the drug. In some examples, at least 5 mol % (e.g., at least 10 mol % or at least 25 mol %) of an atom (e.g., a hydrogen, carbon, nitrogen, or oxygen atom) in a compound described herein is substituted with a stable isotope. For example, at least 50 mol %, 60 mol %, 70 mol %, 80 mol %, or 90 mol % of an atom in a compound as described herein can be substituted with a stable isotope. Isotopic substitution or enrichment can be achieved, for example, by exchanging protons with deuterium or by synthesizing the molecule with enriched or substituted starting materials. Other methods known in the art can also be used for isotopic substitutions.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure.

Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^{1}H$ or $^{13}C$) infrared spectroscopy, spectrophotometry (e.g., UV-visible), or mass spectrometry, or by chromatography such as high performance liquid chromatography (HPLC) or thin layer chromatography.

Exemplary methods for synthesizing compounds as described herein are provided in Example 1 below.

III. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington: The Science and Practice of Pharmacy, 22d Edition, Loyd et al. eds., Pharmaceutical Press and Philadelphia College of Pharmacy at University of the Sciences (2012). Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or non-aqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, inhalants, and skin patches. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

Optionally, the compounds described herein can be contained in a drug depot. A drug depot comprises a physical structure to facilitate implantation and retention in a desired site (e.g., a synovial joint, a disc space, a spinal canal, abdominal area, a tissue of the patient, etc.). The drug depot can provide an optimal concentration gradient of the compound at a distance of up to about 0.1 cm to about 5 cm from the implant site. A depot, as used herein, includes but is not limited to capsules, microspheres, microparticles, microcapsules, microfibers particles, nanospheres, nanoparticles, coating, matrices, wafers, pills, pellets, emulsions, liposomes, micelles, gels, antibody-compound conjugates, protein-compound conjugates, or other pharmaceutical delivery compositions. Suitable materials for the depot include pharmaceutically acceptable biodegradable materials that are preferably FDA approved or GRAS materials. These materials can be polymeric or non-polymeric, as well as synthetic or naturally occurring, or a combination thereof. The depot can optionally include a drug pump.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., J. Pharm. Sci. (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.0001 to about 200 mg/kg of body weight of active compound per day, which may be administered in a single dose or in the form of individual divided doses, such as from 1 to 4 times per day. Alternatively, the dosage amount can be from about 0.01 to about 150 mg/kg of body weight of active compound per day, about 0.1 to 100 mg/kg of body weight of active compound per day, about 0.5 to about 75 mg/kg of body weight of active compound per day, about 0.5 to about 50 mg/kg of body weight of active compound per day, about 0.01 to about 50 mg/kg of body weight of active compound per day, about 0.05 to about 25 mg/kg of body weight of active compound per day, about 0.1 to about 25 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, about 5 mg/kg of body weight of active compound per day, about 2.5 mg/kg of body weight of active compound per day, about 1.0 mg/kg of body weight of active compound per day, or about 0.5 mg/kg of body weight of active compound per day, or any range derivable therein. Optionally, the dosage amounts are from about 0.01 mg/kg to about 10 mg/kg of body weight of active compound per day. Optionally, the dosage amount is from about 0.01 mg/kg to about 5 mg/kg. Optionally, the dosage amount is from about 0.01 mg/kg to about 2.5 mg/kg.

Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The precise dose to be employed in the formulation will also depend on the route of administration, and the seriousness of the disease or disorder, and should be decided according to the judgment of the practitioner and each subject's circumstances. Effective doses can be extrapolated from dose-response curves derived from in vitro or animal model test systems. Further, depending on the route of administration, one of skill in the art would know how to determine doses that result in a plasma concentration for a desired level of response in the cells, tissues and/or organs of a subject.

IV. Methods of Use

Provided herein are methods to treat, prevent, or ameliorate a steroid receptor coactivator-related disease in a subject. The methods include administering to a subject an effective amount of one or more of the compounds or compositions described herein, or a pharmaceutically acceptable salt or prodrug thereof. Effective amount, when used to describe an amount of compound in a method, refers to the amount of a compound that achieves the desired pharmacological effect or other biological effect. The effective amount can be, for example, the concentrations of compounds at which SRC is inhibited or stimulated in vitro, as provided herein. Also contemplated is a method that includes administering to the subject an amount of one or more compounds described herein such that an in vivo concentration at a target cell in the subject corresponding to the concentration administered in vitro is achieved.

The compounds and compositions described herein or pharmaceutically acceptable salts thereof are useful for treating steroid receptor coactivator-related diseases in humans, including, without limitation, pediatric and geriatric populations, and in animals, e.g., veterinary applications.

Optionally, the steroid receptor coactivator-related disease is an SRC-1 related disease. Optionally, the steroid receptor coactivator-related disease is an SRC-2 related disease. Optionally, the steroid receptor coactivator-related disease is an SRC-3 related disease.

In some embodiments, the steroid receptor coactivator-related disease is cancer. Optionally, the cancer is a poor prognosis cancer. The term poor prognosis, as used herein, refers to a prospect of recovery from a disease, infection, or medical condition that is associated with a diminished likelihood of a positive outcome. In relation to a disease such as cancer, a poor prognosis may be associated with a reduced patient survival rate, reduced patient survival time, higher likelihood of metastatic progression of said cancer cells, and/or higher likelihood of chemoresistance of said cancer cells. Optionally, a poor prognosis cancer can be a cancer associated with a patient survival rate of 50% or less. Optionally, a poor prognosis cancer can be a cancer associated with a patient survival time of five years or less after diagnosis. In some embodiments, the cancer is an invasive cancer.

Optionally, the cancer is a cancer that has an increased expression of SRC-1, SRC-2, and/or SRC-3 as compared to non-cancerous cells of the same cell type. Optionally, the cancer is bladder cancer, brain cancer, breast cancer, bronchus cancer, colorectal cancer (e.g., colon cancer, rectal cancer), cervical cancer, chondrosarcoma, endometrial cancer, gastrointestinal cancer, gastric cancer, genitourinary cancer, head and neck cancer, hepatic cancer, hepatocellular carcinoma, leukemia, liver cancer, lung cancer, lymphoma, melanoma of the skin, ovarian cancer, pancreatic cancer, prostate cancer, renal cancer, skin cancer, testicular cancer, thyroid cancer, or uterine cancer. Optionally, the cancer is a cancer that affects one or more of the following sites: oral cavity and pharynx (e.g., tongue, mouth, pharynx, or other oral cavity); digestive system (e.g., esophagus, stomach, small intestine, colon, rectum, anus, anal canal, anorectum, liver and intrahepatic bile duct, gallbladder and other biliary, pancreas, or other digestive organs); respiratory system (e.g., larynx, lung and bronchus, or other respiratory organs); bones and joints; soft tissue (e.g., heart); skin (e.g., melanoma of the skin or other nonepithelial skin); breast; genital system (e.g., uterine cervix, uterine corpus, ovary, vulva, vagina and other female genital areas, prostate, testis, penis and other male genital areas); urinary system (e.g., urinary bladder, kidney and renal pelvis, and ureter and other urinary organs); eye and orbit; brain and other nervous system; endocrine system (e.g., thyroid and other endocrine); lymphoma (e.g., Hodgkin lymphoma and non-Hodgkin lymphoma); myeloma; or leukemia (e.g., acute lymphocytic leukemia, chronic lymphocytic leukemia, acute myeloid leukemia, chronic myeloid leukemia, or other leukemia).

Optionally, the breast cancer is triple negative breast cancer. As used herein, triple negative breast cancer (TNBC) refers to a subtype of breast cancer that lacks detectable protein expression of the estrogen receptor (ER) and progesterone receptor (PR) and the absence of HER2 protein over expression. In other words, TNBC refers to an immunophenotype of breast cancer that is immunologically negative to ER, PR, and HER2.

Optionally, the cancer is glioblastoma. In some examples, the glioblastoma is a glioblastoma multiforme tumor. Optionally, the glioblastoma multiforme tumor is a pediatric glioblastoma multiforme tumor. The methods of treating glioblastoma include administering to the subject a compound as described herein. Optionally, the methods of treating glioblastoma include methods of suppressing the growth of glioblastoma cells in the subject.

In some embodiments, the steroid receptor coactivator-related disease is a metabolic disorder (e.g., obesity, diabetes, and genetic disorders). In some embodiments, the steroid receptor coactivator-related disease is human immunodeficiency virus (HIV). Optionally, the HIV is HIV type 1 (HIV-1). Optionally, the HIV is HIV type 2 (HIV-2). Optionally, the steroid receptor coactivator-related disease is a neurodegenerative disorder. Optionally, the steroid receptor coactivator-related disease is an inflammatory disease. In some embodiments, the steroid receptor coactivator-related disease is a disease as described in Dasgupta et al., Annu Rev Med., 65:279-292 (2014), which is incorporated herein by reference.

The methods of treating or preventing an SRC-related disease (e.g., cancer) in a subject can further comprise administering to the subject one or more additional agents. The one or more additional agents and the compounds described herein or pharmaceutically acceptable salts or prodrugs thereof can be administered in any order, including concomitant, simultaneous, or sequential administration. Sequential administration can be administration in a temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Additional therapeutic agents include, but are not limited to, chemotherapeutic agents, anti-depressants, anxiolytics, antibodies, antivirals, steroidal and non-steroidal anti-inflammatories, conventional immunotherapeutic agents, cytokines, chemokines, and/or growth factors.

A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, bexarotene, gefitinib, erlotinib, gemcitabine, paclitaxel, docetaxel, topotecan, irinotecan, temozolomide, carmustine, vinorelbine, capecitabine, leucovorin, oxaliplatin, bevacizumab, cetuximab, panitumumab, bortezomib, oblimersen, hexamethylmelamine, ifosfamide, CPT-11, deflunomide, cycloheximide, dicarbazine, asparaginase, mitotant, vinblastine sulfate, carboplatin, colchicine, etoposide, melphalan, 6-mercaptopurine, teniposide, vinblastine, antibiotic derivatives (e.g. anthracyclines such as doxorubicin, liposomal doxorubicin, and diethylstilbestrol doxorubicin, bleomycin, daunorubicin, and dactinomycin); antiestrogens (e.g., tamoxifen); antimetabolites (e.g., fluorouracil (FU), 5-FU, methotrexate, floxuridine, interferon alpha-2B, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, vincristine and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chlorambucil, mechlorethamine (nitrogen mustard) and thiotepa); and steroids (e.g., bethamethasone sodium phosphate).

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

Optionally, a compound or therapeutic agent as described herein may be administered in combination with a radiation therapy, an immunotherapy, a gene therapy, or a surgery.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of a steroid receptor coactivator-related disease), during early onset (e.g., upon initial signs and symptoms of a steroid receptor coactivator-related disease), or after the development of a steroid receptor coactivator-related disease. Prophylactic administration can occur for several days to years prior to the manifestation of symptoms of a steroid receptor coactivator-related disease. Therapeutic treatment involves administering to a subject a therapeutically effective amount of the compounds and compositions or pharmaceutically acceptable salts thereof as described herein after a steroid receptor coactivator-related disease is diagnosed.

The compounds described herein are also useful in modulating a steroid receptor coactivator protein in a cell. The methods of modulating a steroid receptor coactivator protein in a cell includes contacting a cell with an effective amount of one or more of the compounds as described herein. Optionally, the steroid receptor coactivator protein is one or more of SRC-1, SRC-2, or SRC-3. Optionally, the contacting is performed in vivo. Optionally, the contacting is performed in vitro.

The methods herein for prophylactic and therapeutic treatment optionally comprise selecting a subject with or at risk of developing a steroid receptor coactivator-related disease. A skilled artisan can make such a determination using, for example, a variety of prognostic and diagnostic methods, including, for example, a personal or family history of the disease or condition, clinical tests (e.g., imaging, biopsy, genetic tests), and the like. Optionally, the methods herein can be used for preventing relapse of cancer in a subject in remission (e.g., a subject that previously had cancer).

V. Kits

Also provided herein are kits for treating or preventing cancer in a subject. A kit can include any of the compounds or compositions described herein. For example, a kit can include a compound of Formula I, Formula II, Formula III, Formula IV, Formula V, Formula VI, Formula VII, Formula VIII, Formula IX, Formula X, Formula XI, Formula XII, Formula XIII, and Formula XIV, one or more tautomers thereof, or mixtures thereof. A kit can further include one or more additional agents, such as one or more chemotherapeutic agents. A kit can include an oral formulation of any of the compounds or compositions described herein. A kit can include an intravenous formulation of any of the compounds or compositions described herein. A kit can additionally include directions for use of the kit (e.g., instructions for treating a subject), a container, a means for administering the compounds or compositions (e.g., a syringe), and/or a carrier.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. As used herein, control refers to the untreated condition (e.g., the tumor cells not treated with the compounds and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

Example 1: Synthesis of Compounds

All chemicals were purchased from Sigma-Aldrich (Milwaukee, Wis.) or Alfa Aesar (Ward Hill, Mass.) unless otherwise specified. All other solvents and reagents were used as obtained without further purification. Compounds were characterized by $^1$H-NMR on a Varian 400-MR spectrometer (Palo Alto, Calif.). Chemical shifts (δ) were given in ppm with reference to solvent signals [$^1$H NMR: DMSO-d6 (2.50)]. UV-Vis measurements were performed in 10×10 mm quartz cuvettes with a Cary 60 UV-Vis Spectrometer. Flash chromatography was performed on a Teledyne ISCO CombiFlash Rf 200. ESI mass spectrometry was measured on an Agilent Mass Spectrometer (6130 single quad).

Compounds as described herein were prepared according to the methods described below. In some cases, the synthesized compounds exist as tautomeric mixtures.

Synthesis of Compound SI-3:

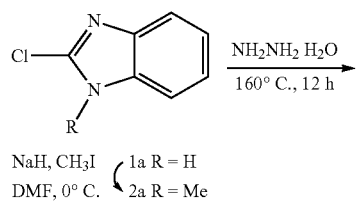

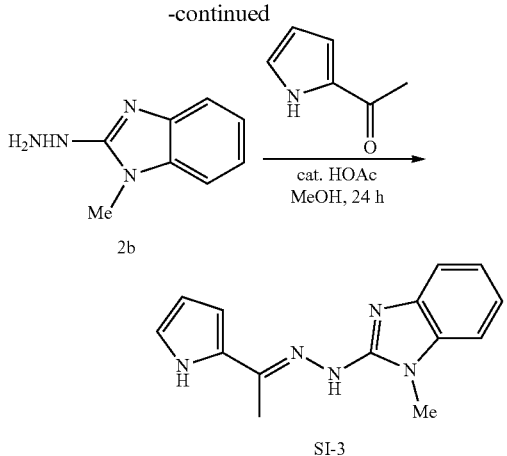

To a solution of 2-chloro-1H-benzo[d]imidazole (916 mg, 6 mmol) in 10 mL of dry DMF, which was cooled to 0° C., was carefully added NaH (240 mg, 10.8 mmol) in small portions. The mixture was stirred for 15 minutes at this temperature. Then, methyl iodide (0.41 mL, 6.6 mmol) was added under continuous stirring for an additional 15 minutes. When thin layer chromatography (TLC) showed full conversion, the mixture was poured into 60 mL of water and a white solid precipitated. The precipitate was collected by filtration and dried in vacuo to obtain 2a 650 mg (65%) of pure product as a white solid. $^1$H NMR (400 MHz, DMSO-d$_6$) δ 7.62-7.54 (m, 2H), 7.34-7.27 (m, 1H), 7.27-7.20 (m, 1H), 3.80 (s, 3H).

2-Chloro-1-methyl-1H-benzo[d]imidazole (2a; 650 mg, 3.90 mmol) was heated at 160° C. in a sealed tube with 4 mL of hydrazine hydrate for 12 hours. After cooling to room temperature, the precipitate was filtered and washed several times with water and dried to give compound 2b (230 mg, 36% yield) as a gray solid. $^1$H NMR (400 MHz, DMSO-d$_6$) δ 7.79 (s, 1H), 7.29-7.21 (m, 1H), 7.20-7.13 (m, 1H), 7.01-6.91 (m, 2H), 4.26 (s, 2H), 3.46 (s, 3H).

A mixture of 2-acetylpyridine (0.16 mL, 1.418 mmol) and the hydrazine 2b (230 mg, 1.418 mmol) in methanol containing 2 drops of acetic acid was reacted at room temperature for 72 hours. The solvent was removed. Recrystallization from methanol afforded SI-3 (290 mg, 77%). $^1$H NMR (400 MHz, CDCl$_3$) δ 10.78 (s, 1H), 7.22 (d, J=7.6 Hz, 1H), 7.12 (t, J=7.6 Hz, 1H), 7.08-7.03 (m, 1H), 6.82 (s, 1H), 6.75 (d, J=8.0 Hz, 1H), 6.10-6.00 (m, 2H), 3.50 (s, 3H), 2.22 (s, 3H).

Syntheses of Compounds SI-4 to SI-8:

The syntheses of SI-4 through SI-8 followed a similar procedure as described for SI-3.

SI-4: $^1$H NMR (400 MHz, CDCl$_3$) δ 7.10-6.96 (m, 5H), 6.87 (s, 1H), 3.95 (s, 3H), 3.52 (s, 3H), 2.54 (s, 3H).

SI-5 (Z, E mixture (4:6)): $^1$H NMR (400 MHz, CDCl$_3$) δ 9.77 (s, 0.6×1H), 9.44 (s, 0.4×Z1H), 7.66 (s, 1H), 7.23-7.18 (m, 1H), 7.15-6.91 (m, 4H), 3.55 (s, 0.6×3H), 3.43 (s, 0.4×3H), 2.50 (s, 3H).

SI-6: $^1$H NMR (400 MHz, CDCl$_3$) δ 8.79 (br s, 1H), 7.82 (d, J=3.2 Hz, 1H), 7.22 (d, J=3.2 Hz, 1H), 7.18-6.95 (m, 4H), 3.57 (s, 3H), 2.57 (s, 3H).

SI-7: $^1$H NMR (400 MHz, CDCl$_3$) δ 9.01 (s, 1H), 7.44 (s, 1H), 7.10-6.91 (m, 4H), 6.70 (d, J=3.2 Hz, 1H), 6.47-6.38 (m, 1H), 3.60 (s, 3H), 2.42 (s, 3H).

SI-8: $^1$H NMR (400 MHz, CDCl$_3$) δ 9.33 (br s, 1H), 7.25-7.19 (m, 2H), 7.15-6.96 (m, 5H), 3.62 (s, 3H), 2.48 (s, 3H).

Synthesis of Compounds SI-9 to SI-21:

Compounds SI-9 through SI-21 were prepared by reacting a hydrazine (5a, 5b, or 5c) with a ketone (6a, 6b, 6c, or 6d). In some cases, the synthesized compounds exist as tautomeric mixtures. Detailed below are the procedures for preparing the hydrazines and for reacting the hydrazines with the ketones.

Synthesis of Hydrazine 5b:

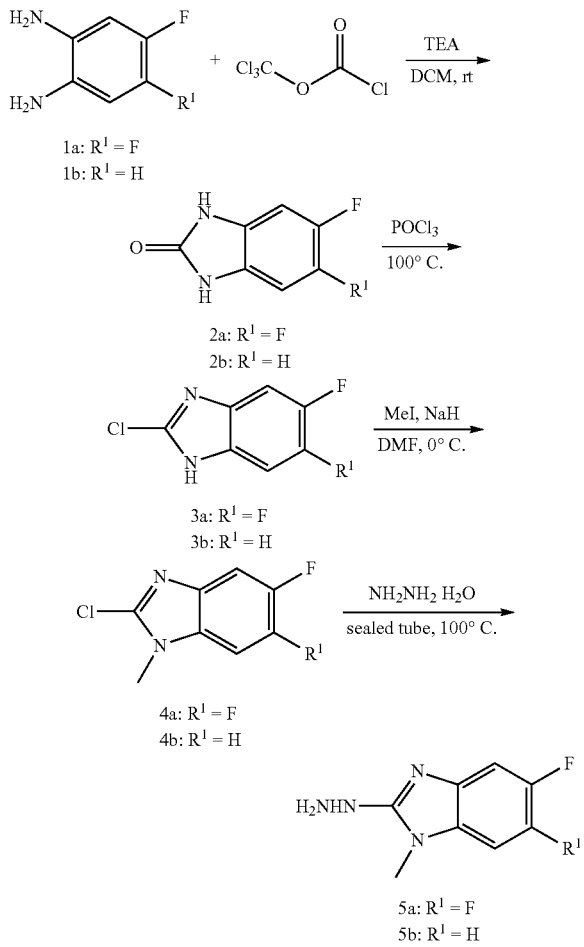

To a solution of 4-fluorobenzene-1,2-diamine 1b (1.39 g, 11.0 mmol) and triethylamine (3.26 mL, 23.2 mmol) in methylene chloride (20 mL) was added dropwise a solution of diphosgene (0.69 mL, 5.72 mmol) in methylene chloride (5 mL) at 0 to 5° C. The resulting suspension was stirred for 2 hours at room temperature and filtered. The collected white solid was washed with water and dried to give compound 2b (1.56 g, 93%). $^1$H NMR (400 MHz, DMSO-$d_6$) δ 10.73 (s, 1H), 10.61 (s, 1H), 6.97-6.81 (m, 1H), 6.74 (m, 2H); MS (ESI): m/z 153.1 [M+1]$^+$.

A solution of 5-fluoro-1,3-dihydro-2H-benzo[d]imidazol-2-one 2b (1.562 g, 10.3 mmol) in phosphorus oxychloride (14 mL, 154.5 mmol) was heated for 18 hours at 100° C. The reaction mixture was cooled to room temperature and excess of POCl$_3$ was evaporated in vacuo. The residue was neutralized with saturated NaHCO$_3$ solution (10 mL) and extracted with EtOAc (3×20 mL). The organic phase was washed with brine and then dried over MgSO$_4$, filtered, and concentrated under reduced pressure to afford 2-chloro-6-fluoro-1H-benzo[d]imidazole 3b (1.552 g, 88%). $^1$H NMR (400 MHz, DMSO-$d_6$) δ 7.51 (s, 1H), 7.34 (d, J=7.6 Hz, 1H), 7.08 (m, 1H); MS (ESI): m/z 171.0 [M+1]$^+$.

To a solution of NaH (546 mg, 60% dispersion in mineral oil) in DMF (10 mL) was added 2-chloro-6-fluoro-1H-benzo[d]imidazole 3b (1.552 g, 9.09 mmol) in DMF (10 mL), at 0° C. The mixture was stirred for a further 15 minutes at this temperature. Then methyl iodide (0.74 mL, 11.8 mmol) was added and stirring was continued for additional 15 minutes. When TLC showed full conversion, the mixture was poured into 60 mL water and the compound was extracted with EtOAc. The organic phase was washed with brine and then dried over MgSO$_4$, filtered, and concentrated under reduced pressure. The residue was purified by flash chromatography using (hexane/ethyl acetate=10:1 to 4:1) to afford compound 4b (1.37 g, 82%). 1:1 mixture, z$^1$H NMR (400 MHz, DMSO-$d_6$) δ 7.62 (d, J=7.8 Hz, 1H), 7.59 (d, J=8.5 Hz, 1H), 7.55 (d, J=9.2 Hz, 1H), 7.43 (d, J=9.6 Hz, 1H), 7.19 (t, J=9.4 Hz, 1H), 7.10 (t, J=9.4 Hz, 1H), 3.79 (s, 3H), 3.77 (s, 3H); MS (ESI): m/z 185.0 [M+1]$^+$.

The mixture of compound 4b (771 mg, 4.18 mmol) in hydrazine hydrate (5 mL) was heated at 100° C. in a sealed tube for 12 hours. After cooling to room temperature, the precipitate was filtered off, washed several times with water, and dried to give compound 5b (670 mg, 89%). $^1$H NMR (400 MHz, DMSO-$d_6$) δ 7.19 (dd, J=8.4, 4.8 Hz, 1H), 7.13 (dd, J=8.4, 4.8 Hz, 1H), 7.10 (d, J=10.0 Hz, 1H), 7.03 (d, J=10.0 Hz, 1H), 6.79 (d, J=10.0 Hz, 1H), 6.74 (d, J=9.2 Hz, 1H), 4.28 (s, 2H), 4.28 (s, 2H), 3.46 (s, 3H), 3.46 (s, 3H); MS (ESI): m/z 181.1 [M+1]$^+$.

Synthesis of Hydrazine 5a:

Compound 5a was prepared according to the procedure described above for hydrazine 5b.

2a: $^1$H NMR (400 MHz, DMSO-$d_6$) δ 10.77 (s, 1H), 6.98 (t, J=8.8 Hz, 1H), MS (ESI): m/z [M+1]$^+$.

3a: $^1$H NMR (400 MHz, DMSO-$d_6$) δ 7.68-7.52 (m, 2H), MS (ESI): m/z 189.0 [M+1]$^+$.

4a: $^1$H NMR (400 MHz, CDCl$_3$) δ 7.47 (dd, J=10.4, 7.2 Hz, 1H), 7.10 (dd, J=9.6, 6.8 Hz, 1H), 3.76 (s, 3H); MS (ESI): m/z 203.0 [M+1]$^+$.

5a: $^1$H NMR (400 MHz, DMSO-$d_6$) δ 7.94 (s, 1H), 7.33 (dd, J=10.8, 7.2 Hz, 1H), 7.23 (dd, J=11.6, 7.2 Hz, 1H), 4.28 (s, 2H), 3.45 (s, 3H); MS (ESI): m/z 199.1 [M+1]$^+$.

Reactions of Hydrazines with Ketones to Form Compounds SI-9 to SI-21:

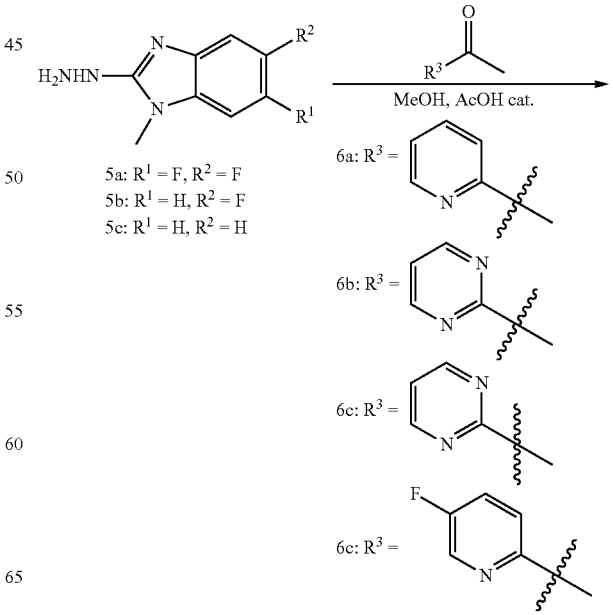

-continued

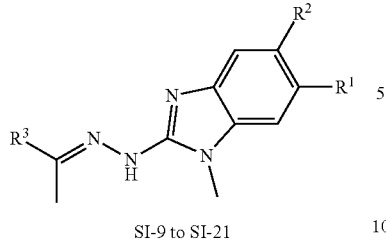

SI-9 to SI-21

General Method:

To the mixture of the hydrazine 5 (0.2 mmol) and ketone 6 (0.21 mmol) in methanol (2 mL) was added acetic acid (2.4 mg, 0.04 mmol) at room temperature. The mixture was stirred for further 12 hours at this temperature. The solvent was removed, and the residue was purified by flash chromatography using (DCM/EtOH=20:1 to 10:1) to afford SI compounds.

SI-9: $^1$H NMR (400 MHz, DMSO-$d_6$) δ 11.14 (s, 1H), 8.54 (d, J=4.4 Hz, 1H), 8.41 (d, J=6.8 Hz, 1H), 7.77 (t, J=7.2 Hz, 1H), 7.47-7.33 (m, 1H), 7.33-7.23 (m, 1H), 7.10-6.98 (m, 1H), 3.43 (s, 3H), 2.40 (s, 3H); MS (ESI): m/z 302.1 [M+1]$^+$.

SI-10: $^1$H NMR (400 MHz, DMSO-$d_6$) δ 11.14 (s, 1H), 8.81 (s, 1H), 8.82 (s, 1H), 7.49-7.30 (m, 2H), 7.10 (dd, J=9.2, 8.0 Hz, 1H), 3.46 (s, 3H), 2.44 (s, 3H); MS (ESI): m/z 303.1 [M+1]$^+$.

SI-11: $^1$H NMR (400 MHz, DMSO-$d_6$) δ 11.47 (s, 1H), 9.12 (s, 1H), 8.71 (d, J=5.2 Hz, 1H), 8.41 (s, 1H), 7.48 (t, J=8.8 Hz, 1H), 7.13 (t, J=8.0 Hz, 1H), 3.49 (s, 3H), 2.36 (s, 3H); MS (ESI): m/z 303.1 [M+1]$^+$.

SI-12: $^1$H NMR (400 MHz, DMSO-$d_6$) δ 11.20 (s, 1H), 8.60-8.40 (m, 2H), 7.74 (td, J=8.8, 2.8 Hz, 1H), 7.46-7.32 (m, 1H), 7.11-6.97 (m, 1H), 3.43 (s, 3H), 2.39 (s, 3H); MS (ESI): m/z 320.1 [M+1]$^+$.

SI-14: $^1$H NMR (400 MHz, CDCl$_3$) δ 8.57 (d, J=4.4 Hz, 1H), 8.02-7.82 (m, 1H), 7.62 (t, J=7.6 Hz, 1H), 7.22-7.10 (m, 1H), 6.99-6.74 (m, 2H), 6.74-6.66 (m, 1H), 3.60 (s, 0.5*3H), 3.56 (s, 0.5*3H), 2.53 (s, 3H); MS (ESI): m/z 284.1 [M+1]$^+$.

SI-15: $^1$H NMR (400 MHz, DMSO-$d_6$) δ 11.04 (s, 1H), 8.81 (s, 1H), 8.80 (s, 1H), 7.36 (m, 1H), 7.14 (d, J=8.4 Hz, 1H), 7.10-6.71-6.90 (m, 1H), 6.85-6.72 (m, 1H), 3.46 (s, 3H), 2.43 (s, 3H); MS (ESI): m/z 285.1 [M+1]$^+$.

SI-16: $^1$H NMR (400 MHz, DMSO-$d_6$) δ 11.50 (s, 0.54*1H), 11.38 (s, 0.45*1H), 9.11 (s, 1H), 8.70 (d, J=5.6 Hz, 1H), 8.44 (s, 1H), 7.27-7.19 (m, 1H), 7.13-6.92 (m, 1H), 6.91-6.81 (m, 1H), 3.50 (s, 3H), 2.36 (s, 3H); MS (ESI): m/z 285.1 [M+1]$^+$.

SI-17: $^1$H NMR (400 MHz, DMSO-$d_6$) δ 11.24 (s, 0.5*1H), 11.10 (s, 0.5*1H), 8.62-8.45 (m, 2H), 7.80-7.65 (m, 1H), 7.14 (d, J=8.8 Hz, 1H), 7.07-6.85 (m, 1H), 6.95-6.71 (m, 1H), 3.45 (s, 3H), 2.39 (s, 3H); MS (ESI): m/z 302.1 [M+1]$^+$.

SI-19: $^1$H NMR (400 MHz, CDCl$_3$) δ 11.31 (br s, 1H), 8.73 (s, 1H), 8.72 (s, 1H), 7.14 (t, J=4.8 Hz, 1H), 7.09 (d, J=7.2 Hz, 1H), 7.07-7.03 (m, 2H), 7.03-6.94 (m, 2H), 3.59 (s, 3H), 2.59 (s, 3H); MS (ESI): m/z 267.1 [M+1]$^+$.

SI-20: $^1$H NMR (400 MHz, DMSO-$d_6$) δ 11.40 (s, 1H), 9.10 (s, 1H), 8.68 (d, J=5.2 Hz, 1H), 8.47 (d, J=5.2 Hz, 1H), 7.29-7.22 (m, 1H), 7.20-7.14 (m, 1H), 7.11-7.03 (m, 2H), 3.52 (s, 3H), 2.36 (s, 3H); MS (ESI): m/z 267.1[M+1]$^+$.

SI-21: $^1$H NMR (400 MHz, DMSO-$d_6$) δ 11.12 (s, 1H), 8.56 (dd, J=8.8, 4.8 Hz, 1H), 8.50 (d, J=2.8 Hz, 1H), 7.72 (td, J=8.8, 2.8 Hz, 1H), 7.17 (d, J=6.4 Hz, 1H), 7.13-7.09 (m, 1H), 7.04-6.99 (m, 1H), 6.99-6.94 (d, 1H), 3.46 (s, 3H), 2.40 (s, 3H); MS (ESI): m/z 284.1 [M+1]$^+$.

Example 2: Small Molecule Regulators of Steroid Receptor Coactivators

Described herein is a new class small molecule regulators (i.e., inhibitors and stimulators) of steroid receptor coactivators, which can be applied to treat neurological and metabolic disorders, inflammatory diseases, and cancer.

SI Compounds are Potent in Cancer Cell Lines

The compounds described herein were synthesized as described in Example 1. The $IC_{50}$ values were measured in MDA-MB-468, BT-474, and MCF-7 cells by incubating a series of concentrations of the corresponding compounds for 72 hours. The results are shown in Table 1.

TABLE 1

| Compounds | MDA-MB-468 | BT-474 | MCF-7 |
|---|---|---|---|
| SI-3 | NA* | | |
| SI-4 | NA* | | |
| SI-5 | NA* | | |
| SI-6 | ++ | | |
| SI-7 | NA* | | |
| SI-8 | NA* | | |
| SI-9 | | +++ | |
| SI-10 | | +++ | +++ |
| SI-11 | | +++ | +++ |
| SI-12 | | +++ | +++ |
| SI-14 | | +++ | +++ |
| SI-15 | | +++ | +++ |
| SI-16 | | +++ | +++ |
| SI-17 | | +++ | +++ |
| SI-19 | | +++ | +++ |
| SI-20 | | +++ | +++ |
| SI-21 | | +++ | +++ |

The $EC_{50}$ values of certain compounds were measured in MDA-MB-468 cells by incubating a series of concentrations of the corresponding compounds for 72 hours. The results are shown in Table 2.

TABLE 2

| Compounds | MDA-MB-468 |
|---|---|
| SI-B-01 | NA* |
| SI-C-01 | ++ |
| SI-D-01 | ++ |
| SI-E-01P | ++ |
| SI-F-01 | NA* |
| SI-H-01 | NA* |
| SI-I-01 | NA* |

In Tables 1 and 2, "−" represents $IC_{50}$ or $EC_{50}$ values greater than 10 μM; "+" represents $IC_{50}$ or $EC_{50}$ values from greater than 1 μM to 10 μM; "++" represents $IC_{50}$ or $EC_{50}$ values from 0.1 μM to 1 μM; and "+++" represents $IC_{50}$ or $EC_{50}$ values less than 0.1 μM. Also in Tables 1 and 2, "*" indicates no appreciate cell death was observed at a compound concentration of 500 nM.

SI Compounds Regulate Intrinsic Transcriptional Activities of SRCs

Figure 2:
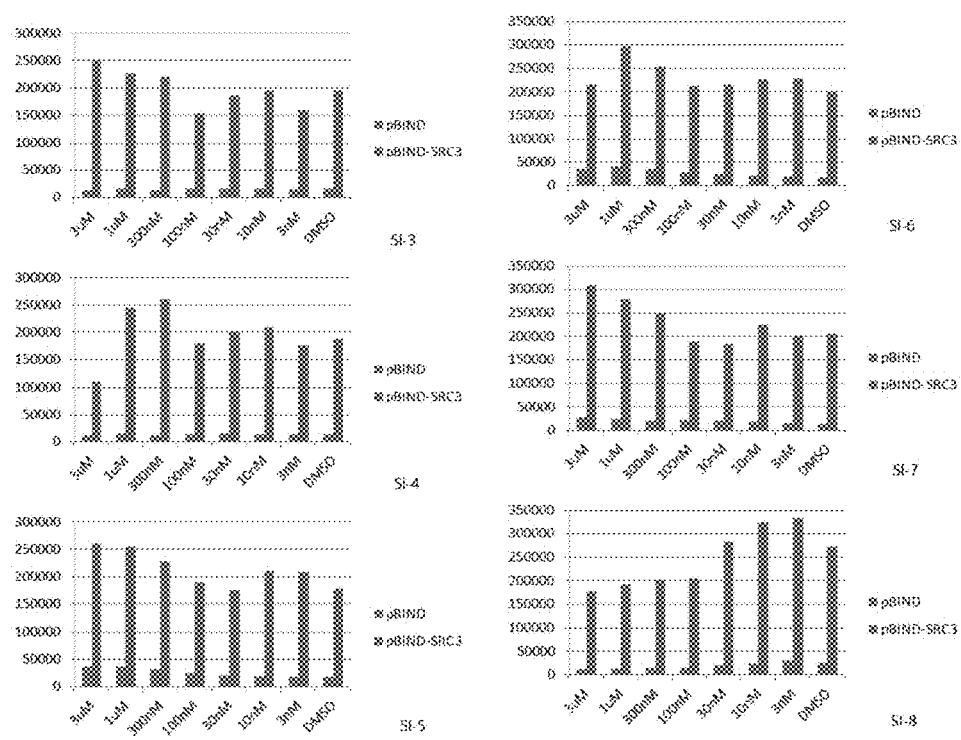
FIG. 2 shows that a series of compounds were able to stimulate SRC-3 intrinsic activity at certain doses. Intrinsic transcriptional activity assays were conducted as for FIG. 1.

The effects of the SI compounds described herein on the intrinsic transcriptional activities of SRC-1, SRC-2 and SRC-3 were investigated. HeLa cells were transiently transfected with a pGL5-LUC reporter and expression vectors for pBIND and pBIND-SRC-1, pBIND-SRC-2, pBIND-SRC-3, followed by 24 hours of treatment with different concentrations of SI compounds. Compounds as described herein, including SI-9, SI-10, SI-11, SI-12, SI-14, SI-15, SI-16, SI-17, SI-19, SI-20, and SI-21, were tested for their ability to inhibit the intrinsic transcriptional activity of SRC-1, SRC-2 and SRC-3 in FIG. 1. Some compounds, including SI-3, SI-4, SI-5, SI-6, SI-7, and SI-8, were able to stimulate SRC-3 intrinsic activity at certain doses (FIG. 2).

Example 3

Figure 3:
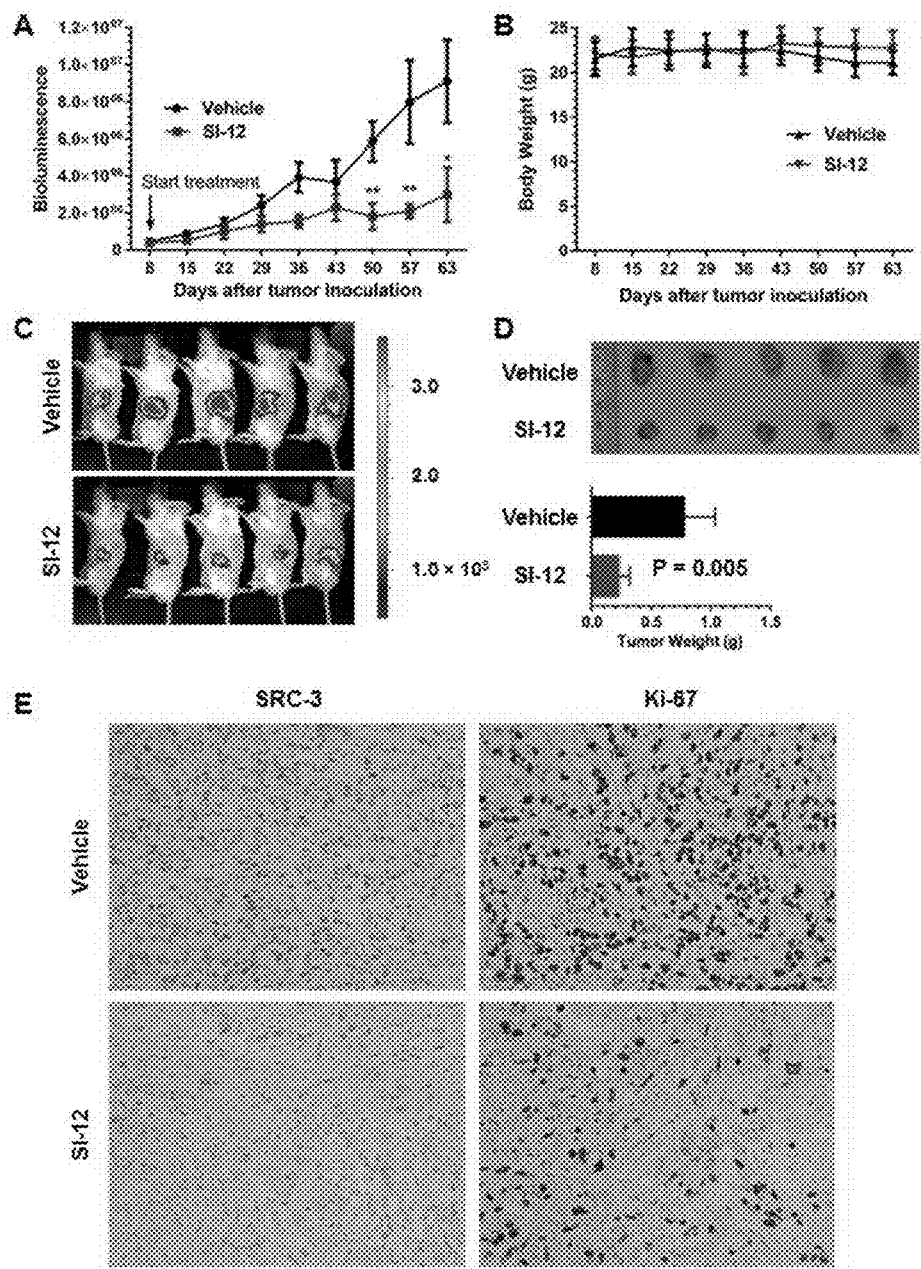
FIG. 3, Panels A-E show the therapeutic efficacy of SI-12 in an orthotopic pancreatic cancer mouse model. Panel (A) shows the luminescence intensities of tumors after treatment with SI-12 or the vehicle. Panel (B) shows the body weights after treatment with SI-12 or the vehicle. Data represent mean±SEM. *, P<0.05, **, P<0.01 by student t-test. Panel (C) shows representative images of luciferase imaging after 8 weeks of treatment with SI-12 or the vehicle. Panel (D) shows the harvested tumors after 8 weeks of treatment with SI-12 or the vehicle and a plot of the tumor weights. Panel (E) shows images of tumor tissues (N>3) collected from the control and the SI-12 groups that were processed and immunohistochemically stained with an anti-SRC-3 antibody or an anti-Ki-67 antibody.

SI-12 was tested in pancreatic, lung, brain, and melanoma cancers. A representative example for pancreatic tumor treatment is described below. Panc-1 cells stably expressing firefly luciferase cells (Panc-1-Luc, $0.5 \times 10^6$ cells per mouse) were injected into the tail of pancreas of SCID mice (6-7 weeks). The mice were randomized into two groups based on luciferase imaging (n=8 per group). Eight days after tumor inoculation, the two groups were administered SI-12 (10 mg/kg, i.p. injection, once daily) or an equal volume of vehicle control five times per week. Tumor growth and systemic toxicity were monitored based on luciferase imaging and body weight weekly. The mice were sacrificed after eight weeks of treatment. SI-12 treatment significantly delayed pancreatic tumor growth (FIGS. 3A and 3C), while causing minimal body weight loss (FIG. 3B). At the end of the experiment, tumors were harvested and weighed. The average tumor weight in SI-12 treated mice was ~30% of the vehicle treated counterparts (FIG. 3D).

To test whether SI-12 causes SRC-3 down-regulation in vivo, the SRC-3 levels in tumor tissues were measured by immunohistochemistry (IHC). Multiple tumor tissues (N>3) collected from both the control group and the SI-12 treated group were processed and immunohistochemically stained with an anti-SRC-3 antibody or an anti-Ki-67 antibody. As shown in FIG. 3E, the SRC-3 levels (dark color) in SI-12 treated tumor tissues were significantly lower than the vehicle treated control group. Ki-67, a cell proliferation marker, was also immunochemically analyzed. The SI-12 treated tumor tissues had dramatically fewer Ki-67 positive cells (the cells with dark staining, FIG. 3E). Based on these data, SI-12 significantly inhibits pancreatic tumor growth through inhibition of SRC-3.

SI-12 was also tested for its ability to disrupt kinase activity. The effects of the compound were tested on a panel of 24 kinases using a Kinase-Glo Luminescent Kinase Assay system (Promega; Madison, Wis.). SI-12 was tested, at concentrations of 1000 nM, 50 nM, and 5 nM, for its ability to interfere with recombinant kinases in the assay system. The amount of ATP to ADP conversion in the presence of SI-12 was compared to a DMSO vehicle control. The values shown in Table 3 represent the percentage of kinase activity compared to a DMSO vehicle control. SI-12 had minimal effects on kinase activity in this biochemical assay system (see Table 3).

TABLE 3

| Kinase | 1000 nM | 50 nM | 5 nM |
| --- | --- | --- | --- |
| AKT1 | − | − | − |
| PKCa | − | − | − |
| ROCK1 | + | + | + |
| Aurora A | − | − | − |
| CK2a 1 | − | − | − |
| IKKb | +++ | +++ | ++ |
| CK1a 1 | − | − | − |
| CK1y1 | − | − | − |
| FGFR1 | − | − | + |
| CDK2/CyclinE1 | − | − | − |

TABLE 3-continued

| Kinase | 1000 nM | 50 nM | 5 nM |
| --- | --- | --- | --- |
| JAK3 | + | + | − |
| GSK3B | − | − | − |
| LCK | − | − | − |
| P38A | − | − | − |
| SYK | − | − | − |
| AMPK A1/B1/G2 | − | − | − |
| MINK1 | − | − | − |
| CAMK4 | − | − | − |
| PAK1/CDC42 | − | − | − |
| CHK1 | − | − | − |
| IRAK4 | − | − | − |
| DAPK1 | − | − | − |
| TAK1-TAB1 | − | − | − |
| MAPKAPK2 | − | − | − |

In Table 3, "−" represents less than 20% inhibition; "+" represents from 20% to 40% inhibition; "++" represents from 40% to 60% inhibition; and "+++" represents greater than 60% inhibition.

Figure 4:
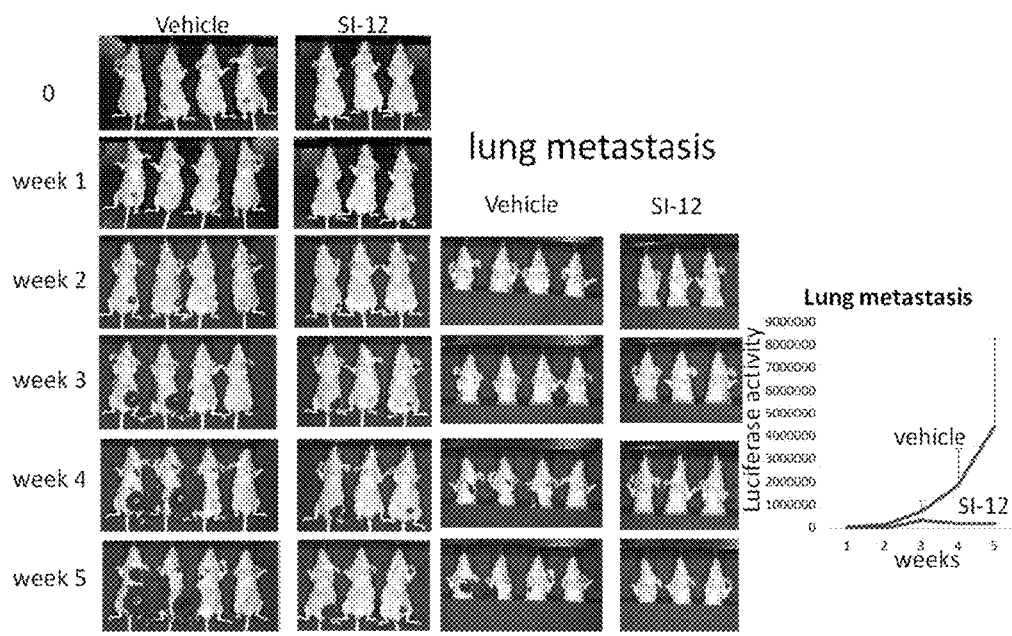
FIG. 4 shows pictures of luciferase imaging of whole mice that had luciferase-expressing MDA-MB-231 triple negative breast cancer (TNBC) tumor cells implanted and were treated with SI-12 or vehicle once per week to track tumor progression. The quantitated luciferase activity is shown in the graph in FIG. 4.

FIG. 4 shows that SI-12 can inhibit tumor growth in a MDA-MB-231 xenograft model. SI-12 was evaluated in a MDA-MB-231 model where the MDA-MB-231 tumor cells were stably transfected with a luciferase expression vector. Nude mice had $2.5 \times 10^5$ tumor cells implanted into cleared mammary fat pads of nude mice. The progression of tumors in control and SI-12 treated animals (4 mg/kg 5 times per week) was followed by luciferase imaging of the mice over a five-week period. It was shown through whole body luciferase imaging that SI-12 reduced luciferase expression at both the sites of the primary tumor and of MDA-MB-231 metastasis to the lung (FIG. 4).

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods are intended to fall within the scope of the appended claims. Thus, a combination of steps, elements, components, or constituents can be explicitly mentioned herein; however, all other combinations of steps, elements, components, and constituents are included, even though not explicitly stated.

What is claimed is:
1. A compound of the following formula:

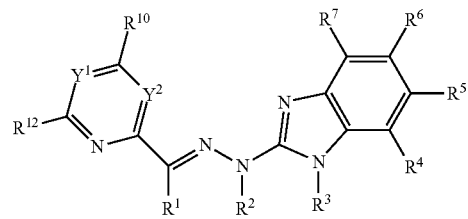

or a pharmaceutically acceptable salt or prodrug thereof, wherein:
$R^1$, $R^4$, $R^5$, $R^6$, and $R^7$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl;

$R^2$ is hydrogen, substituted or unsubstituted alkyl, or substituted or unsubstituted aryl;

$R^3$ is substituted or unsubstituted alkyl or substituted or unsubstituted aryl;

$Y^1$ and $Y^2$ are each independently selected from CR and N, wherein R is hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, or substituted or unsubstituted heterocycloalkyl; and $R^{10}$ and $R^{12}$ are each independently selected from hydrogen, halogen, cyano, trifluoromethyl, substituted or unsubstituted alkyl, substituted or unsubstituted alkenyl, substituted or unsubstituted alkynyl, substituted or unsubstituted heteroalkyl, substituted or unsubstituted heteroalkenyl, substituted or unsubstituted heteroalkynyl, substituted or unsubstituted aryl, substituted or unsubstituted heteroaryl, substituted or unsubstituted cycloalkyl, and substituted or unsubstituted heterocycloalkyl, wherein at least one of $R^4$, $R^5$, $R^6$, and $R^7$ is halogen.

2. The compound of claim 1, wherein R, $R^{10}$, and $R^{12}$ are each independently selected from hydrogen and halogen.

3. The compound of claim 1, wherein the compound is selected from the group consisting of

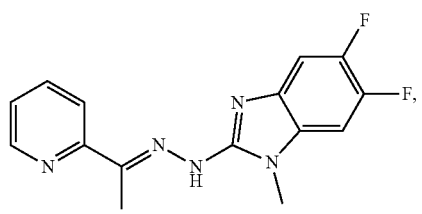

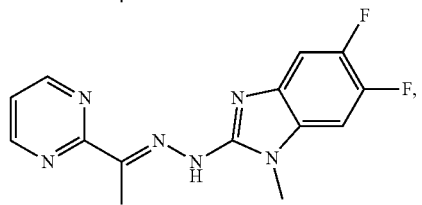

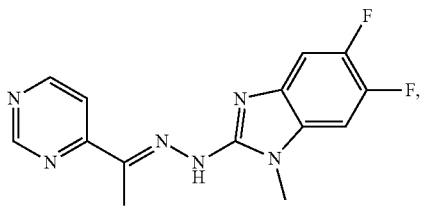

-continued

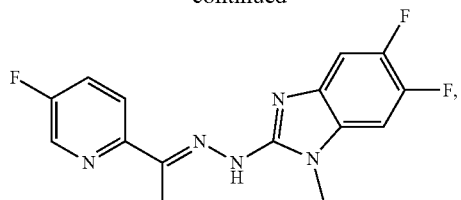

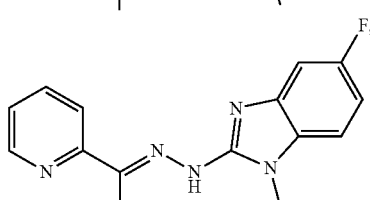

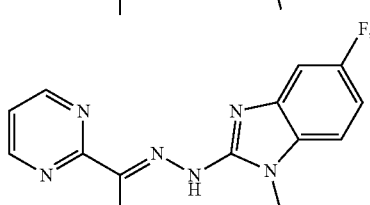

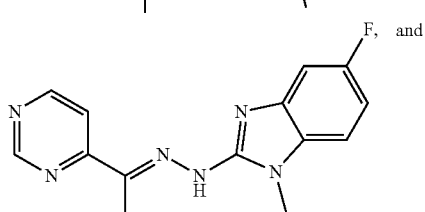

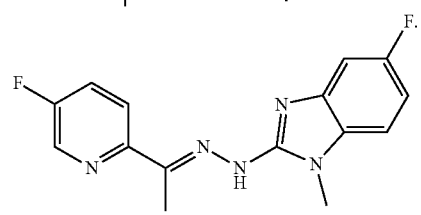

4. A tautomer of the compound of claim 1.

5. The compound of claim 1, wherein the compound is isotopically substituted with a stable isotope.

6. The compound of claim 5, wherein the stable isotope is selected from the group consisting of deuterium, $^{13}C$, $^{15}N$, and $^{18}O$.

7. A composition comprising a compound of claim 1 and a pharmaceutically acceptable carrier.

8. A kit comprising a compound of claim 1.

9. A method of treating a steroid receptor coactivator-related disease in a subject wherein said disease is selected from the group consisting of pancreatic cancer, lung cancer, brain cancer, and melanoma cancer, comprising:
administering to the subject an effective amount of a compound of claim 1.

10. The method of claim 9, further comprising administering a second compound or composition.

11. The method of claim 10, wherein the second compound or composition is a chemotherapeutic agent.

12. A method of regulating a steroid receptor coactivator protein in a cell, comprising:
contacting a cell with an effective amount of a compound of claim 1.

13. The method of claim 12, wherein the steroid receptor coactivator protein is SRC-1, SRC-2, or SRC-3.

14. The method of claim 12, wherein the contacting is performed in vitro or in vivo.

15. The compound of claim 1, wherein at least one of $R^4$, $R^5$, $R^6$, and $R^7$ is fluoro.

16. The compound of claim 1, wherein the compound is:

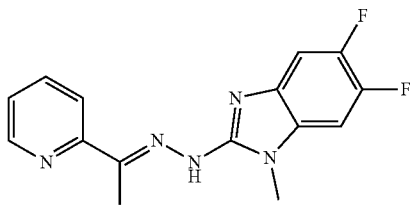 [SMILES: C/C(=N\Nc1nc2cc(F)c(F)cc2n1C)c1ccccn1]

or a pharmaceutically acceptable salt or prodrug thereof.

17. The compound of claim 1, wherein the compound is:

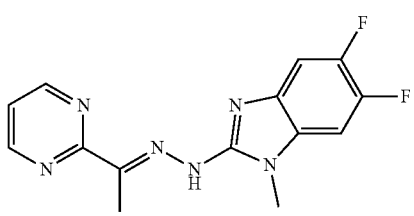 [SMILES: C/C(=N\Nc1nc2cc(F)c(F)cc2n1C)c1ncccn1]

or a pharmaceutically acceptable salt or prodrug thereof.

18. The compound of claim 1, wherein the compound is:

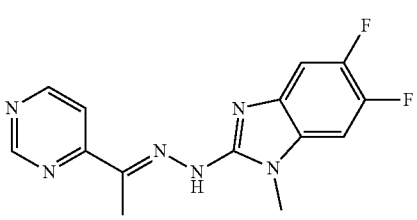 [SMILES: C/C(=N\Nc1nc2cc(F)c(F)cc2n1C)c1ccncn1]

or a pharmaceutically acceptable salt or prodrug thereof.

19. The compound of claim 1, wherein the compound is:

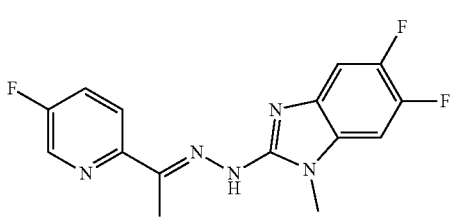

or a pharmaceutically acceptable salt or prodrug thereof.

20. The compound of claim 1, wherein the compound is:

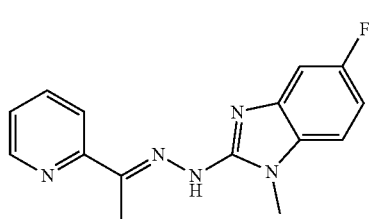 [SMILES: C/C(=N\Nc1nc2cc(F)ccc2n1C)c1ccccn1]

or a pharmaceutically acceptable salt or prodrug thereof.

21. The compound of claim 1, wherein the compound is:

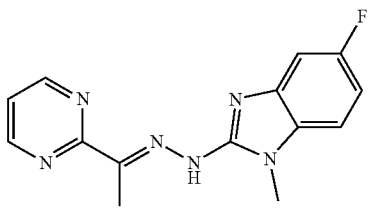 [SMILES: C/C(=N\Nc1nc2cc(F)ccc2n1C)c1ncccn1]

or a pharmaceutically acceptable salt or prodrug thereof.

22. The compound of claim 1, wherein the compound is:

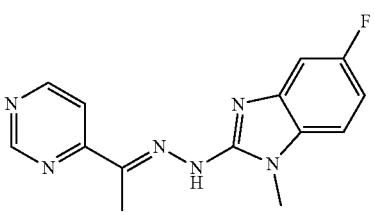 [SMILES: C/C(=N\Nc1nc2cc(F)ccc2n1C)c1ccncn1]

or a pharmaceutically acceptable salt or prodrug thereof.

23. The compound of claim 1, wherein the compound is:

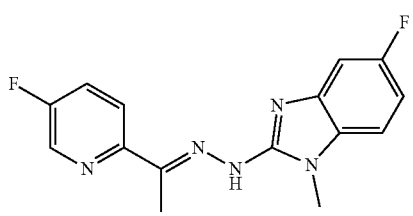 [SMILES: C/C(=N\Nc1nc2cc(F)ccc2n1C)c1ccc(F)cn1]

or a pharmaceutically acceptable salt or prodrug thereof.

24. The compound of claim 1, wherein the compound is in a Z-configuration or an E-configuration.

25. A compound of the following formula:

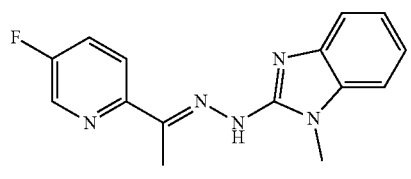 [SMILES: C/C(=N\Nc1nc2ccccc2n1C)c1ccc(F)cn1]

or a pharmaceutically acceptable salt or prodrug thereof.

26. A compound of the following formula:

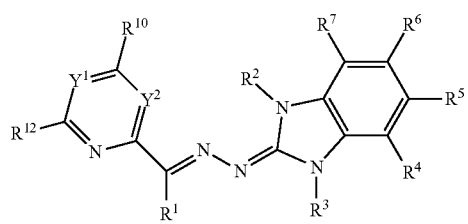

or a pharmaceutically acceptable salt or prodrug thereof, wherein:
$R^1$ is methyl, $R^2$ is methyl or hydrogen, $R^3$ is methyl or hydrogen, $R^4$ is hydrogen, $R^5$ is fluoro, $R^6$ is fluoro, $R^7$ is hydrogen, $Y^1$ is CH or CF, $Y^2$ is CH, $R^{10}$ is hydrogen, and $R^{12}$ is hydrogen;

with the proviso that when $R^2$ is methyl, then $R^3$ is hydrogen and when $R^2$ is hydrogen, then $R^3$ is methyl.

27. The compound of claim 26, wherein the compound is in a Z-configuration or an E-configuration.

* * * * *

UNITED STATES PATENT AND TRADEMARK OFFICE
CERTIFICATE OF CORRECTION

PATENT NO. : 10,265,315 B2
APPLICATION NO. : 15/480731
DATED : April 23, 2019
INVENTOR(S) : Bert W. O'Malley et al.

Page 1 of 1

It is certified that error appears in the above-identified patent and that said Letters Patent is hereby corrected as shown below:

In the Specification

In Column 1 at Lines 18-23, under the heading STATEMENT REGARDING FEDERALLY FUNDED RESEARCH delete:
"This invention was made with government support under Grant Nos. R01GM115622, HD076596, DK059820, and R01CA112403, awarded by the National Institutes of Health, and Grant No. DOD BC120894, awarded by the Department of Defense. The government has certain rights in the invention."

And insert:
--This invention was made with government support under Grant Nos. R01GM115622, HD076596, DK059820, and R01CA112403, awarded by the National Institutes of Health, and Grant No. W81XWH-13-1-0285, awarded by the Department of Defense. The government has certain rights in the invention.--

Signed and Sealed this
Fifth Day of May, 2020

Andrei Iancu
*Director of the United States Patent and Trademark Office*